US012668581B2

(12) United States Patent
Muthusamy et al.

(10) Patent No.: US 12,668,581 B2
(45) Date of Patent: Jun. 30, 2026

(54) PROCESSES FOR THE PREPARATION OF GLASDEGIB AND SALT THEREOF AND SOLID STATE FORMS OF GLASDEGIB MALEATE AND PROCESS FOR PREPARATION THEREOF

(71) Applicant: ASSIA CHEMICAL INDUSTRIES LTD., Tel Aviv (IL)

(72) Inventors: Anantha Rajmohan Muthusamy, Sivakasi (IN); Amit Singh, Greater Noida (IN); Rajendra Popat Chemate, Ahmednagar (IN); Bhatu Tumba Patil, Nandurbar (IN); Elluru Subbi Reddy, Greater Noida (IN); Parven Kumar Luthra, New Delhi (IN); Sanjay Lakhabhai Vasoya, Rajkot (IN); Dnyaneshwar Kondibhau Nighot, Pune (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 1007 days.

(21) Appl. No.: 17/792,193

(22) PCT Filed: Jan. 28, 2021

(86) PCT No.: PCT/US2021/015352

§ 371 (c)(1),
(2) Date: Jul. 12, 2022

(87) PCT Pub. No.: WO2021/154901

PCT Pub. Date: Aug. 5, 2021

(65) Prior Publication Data

US 2023/0107634 A1 Apr. 6, 2023

(30) Foreign Application Priority Data

Jan. 28, 2020 (IN) ............................. 202011003718
Mar. 11, 2020 (IN) ............................. 202011010330
Jun. 26, 2020 (IN) ............................. 202011027219

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC .......................... C07D 401/14; C07B 2200/13
See application file for complete search history.

(56) References Cited

U.S. PATENT DOCUMENTS 5,925,762 A 7/1999 Thavonekham
2018/0086731 A1* 3/2018 Hansen .............. A61K 31/4439

OTHER PUBLICATIONS

Mino R. Caira, "Crystalline Polymorphism of Organic Compounds", Topics in Current Chemistry; vol. 198, Jan. 1, 1998, pp. 163-208, XP001156954.
Michael J. Munchhof, et al. "Discovery of PF-04449913, a Potent and Orally Bioavailable Inhibitor of Smoothened", ACS Medicinal Chemistry Letters, vol. 3, No. 2, Feb. 9, 2012 pp. 106-111, XP055207149.
Peng Zhihui et al, "Development of a Concise, Asymmetric Synthesis of a Smoothened Receptor (SMO) Inhibitor: Enzymatic Transamination of a 4-Piperidinone with Dynamic Kinetic Resolution", Organic Letters, vol. 16, No. 3, Jan. 22, 2014, pp. S1-S19.
Magdalena Litwinowicz et al., "Carbamoylation of primary, secondary and aromatic amines by dimethyl carbonate in a flow system over solid catalysts", Sustainable Chemical Processes, vol. 3, No. 1, Jan. 30, 2015, pp. 1-7, XP021213483.
International Search Report and Written Opinion of the International Searching Authority issued in corresponding application PCT/US2021/015352 mailed Jun. 17, 2021 (19 pages).

* cited by examiner

*Primary Examiner* — Sarah Pihonak
*Assistant Examiner* — Mikhail O'Donnel Robinson
(74) *Attorney, Agent, or Firm* — Carter, DeLuca & Farrell, LLP

(57) ABSTRACT

The present disclosure relates to safe and efficient processes for the synthesis of Glasdegib or salts thereof, preferably Glasdegib Maleate. The present disclosure also encompasses solid state forms of Glasdegib maleate, in embodiments crystalline polymorphs of Glasdegib maleate, processes for preparation thereof, and pharmaceutical compositions thereof.

10 Claims, 13 Drawing Sheets

Figure 1: X-Ray Powder Diffraction Pattern of Glasdegib maleate Form GT1
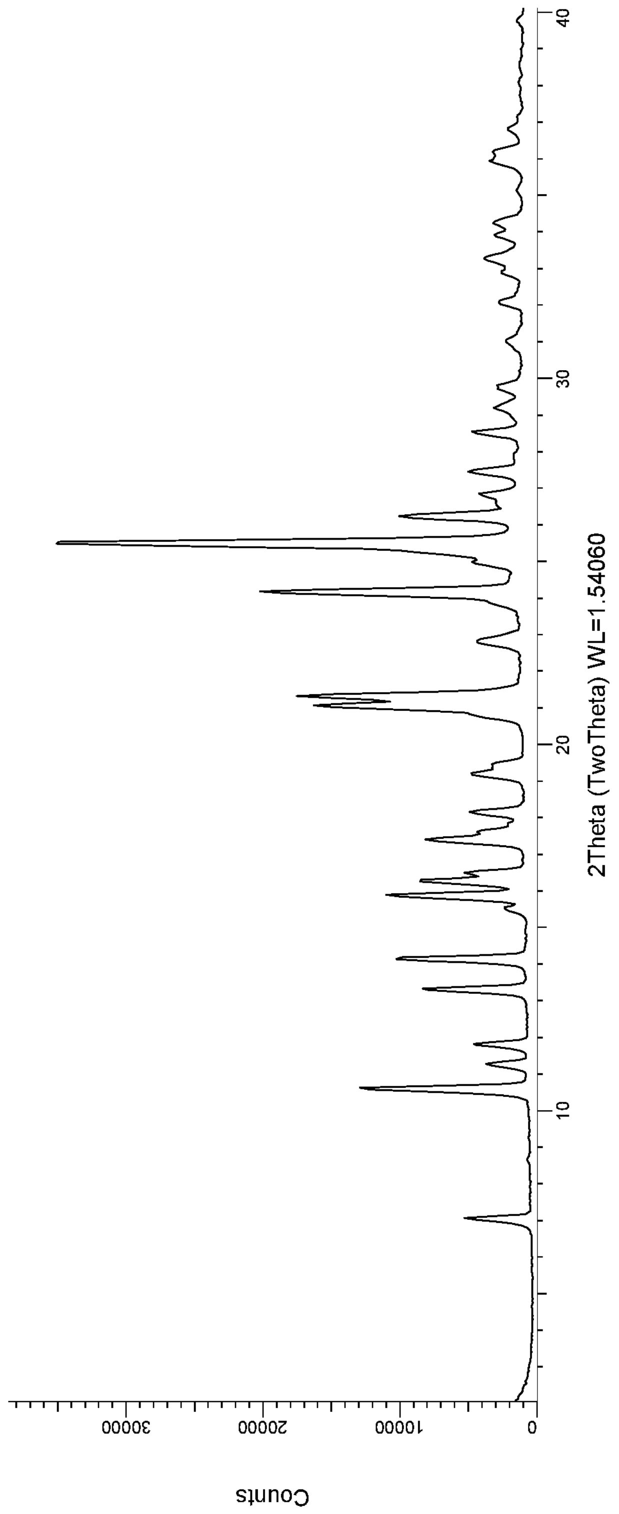

Figure 2: X-Ray Powder Diffraction Pattern of Glasdegib maleate Form GT2
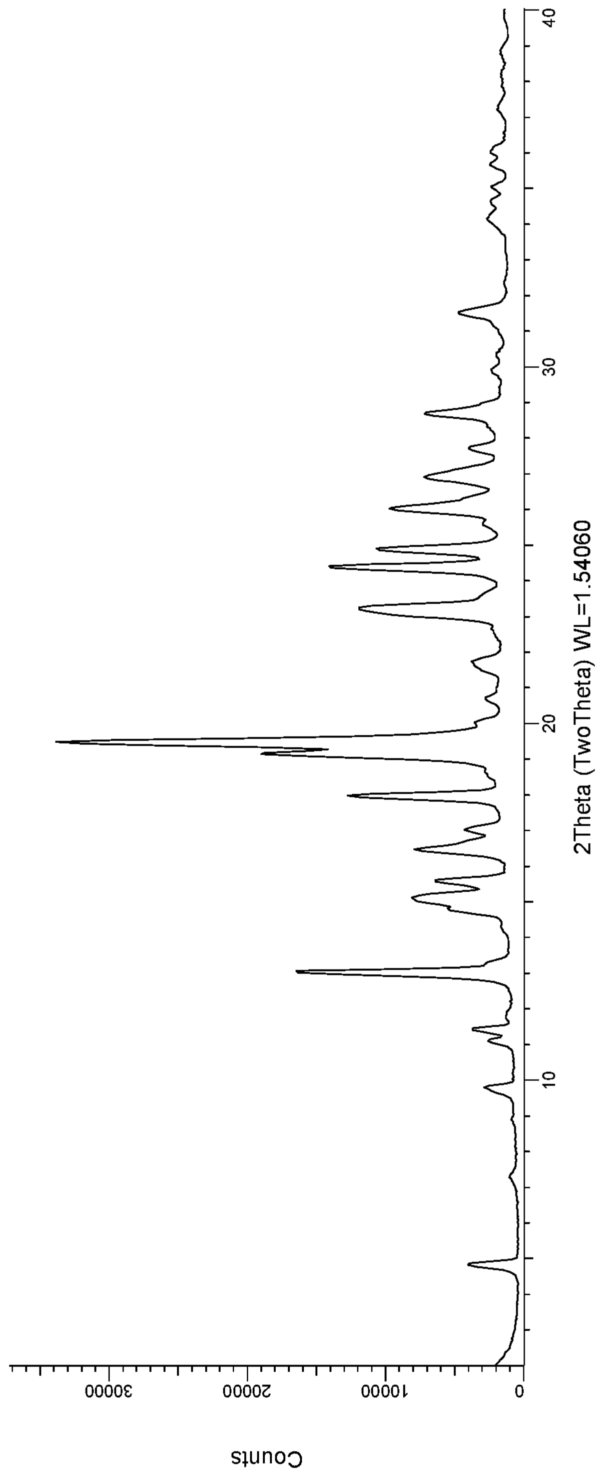

Figure 3: X-Ray Powder Diffraction Pattern of Amorphous Glasdegib maleate
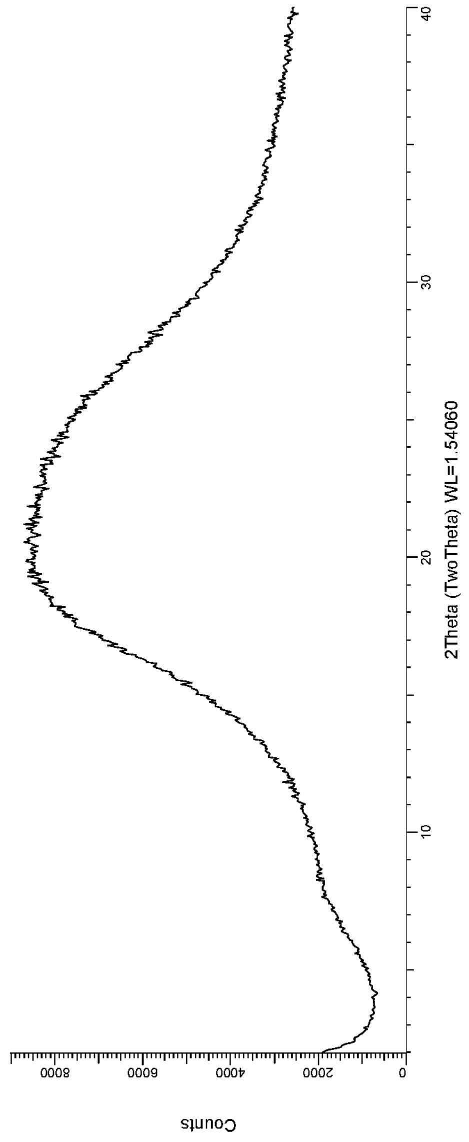

Figure 4: X-Ray Powder Diffraction Pattern of Glasdegib Form A
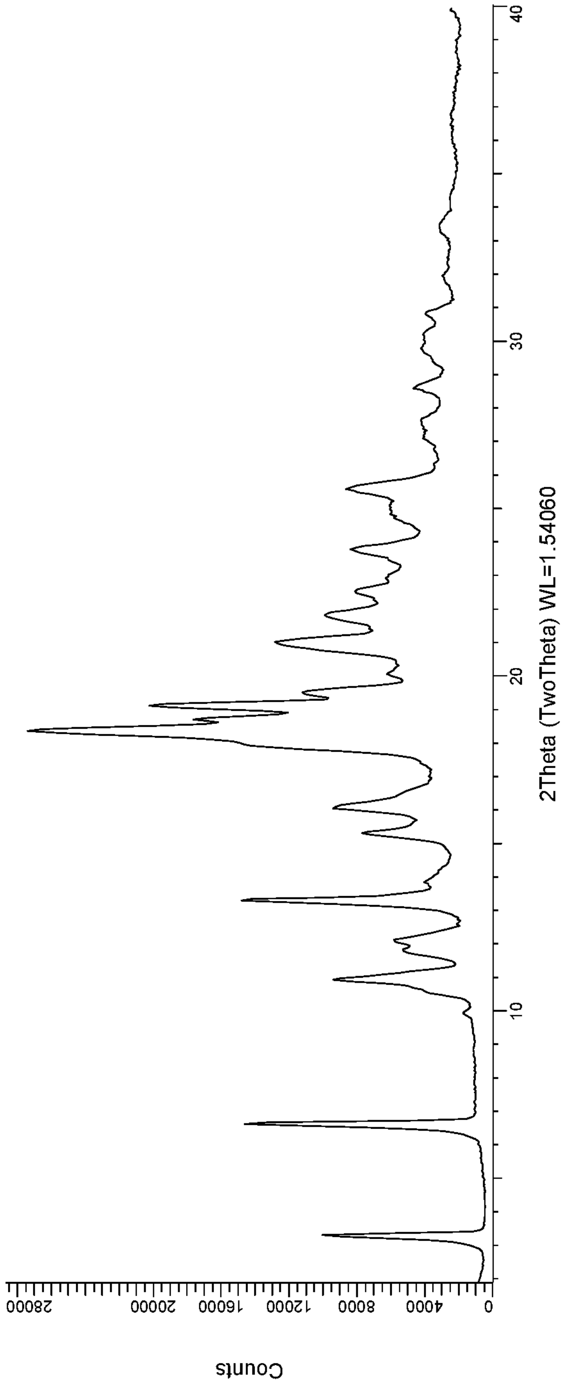

Figure 5: X-Ray Powder Diffraction Pattern of Amorphous Glasdegib
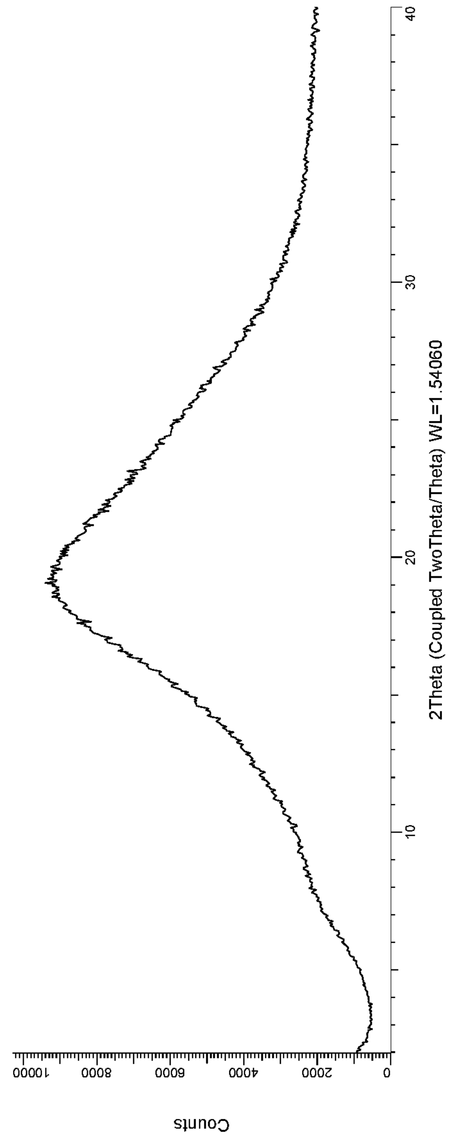

Figure 6: X-Ray Powder Diffraction Pattern of Glasdegib maleate Form GT3
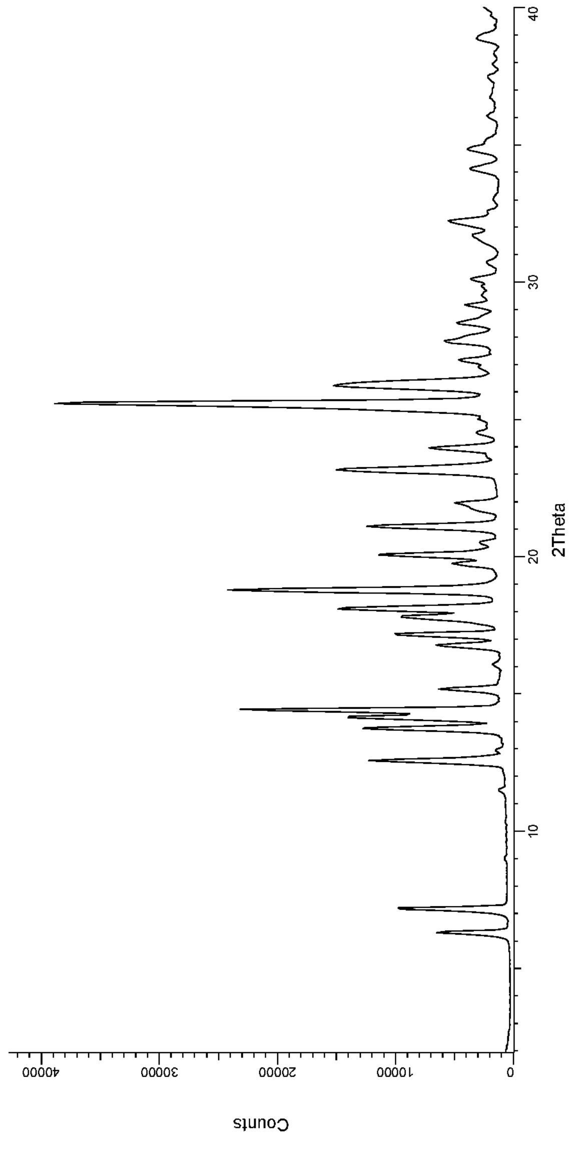

Figure 7: X-Ray Powder Diffraction Pattern of Glasdegib maleate Form GT4
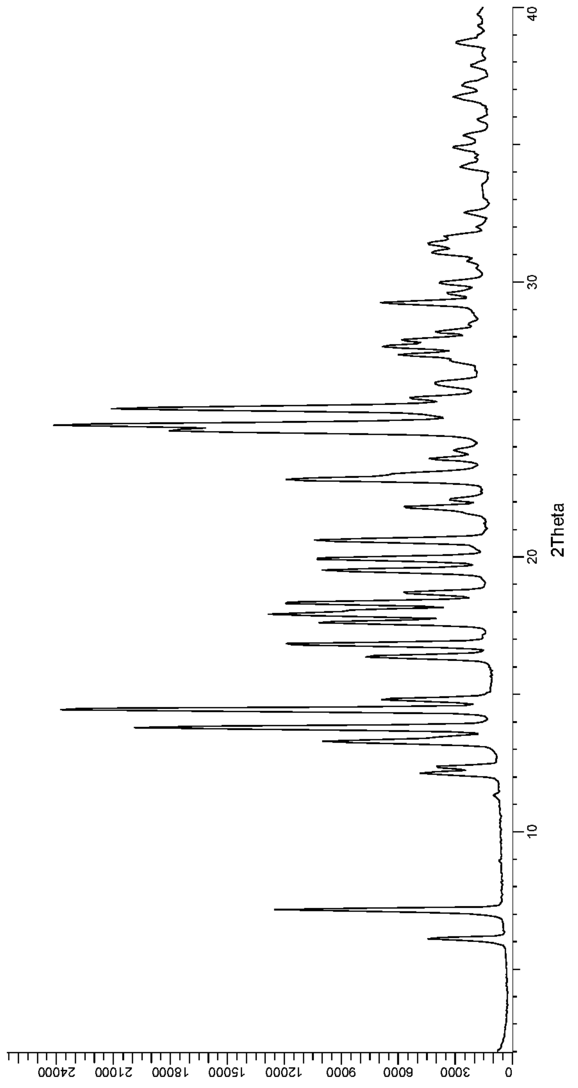

Figure 8a: $^{13}C$ solid state NMR spectrum of Form GT1 of Glasdegib Maleate (full scan)
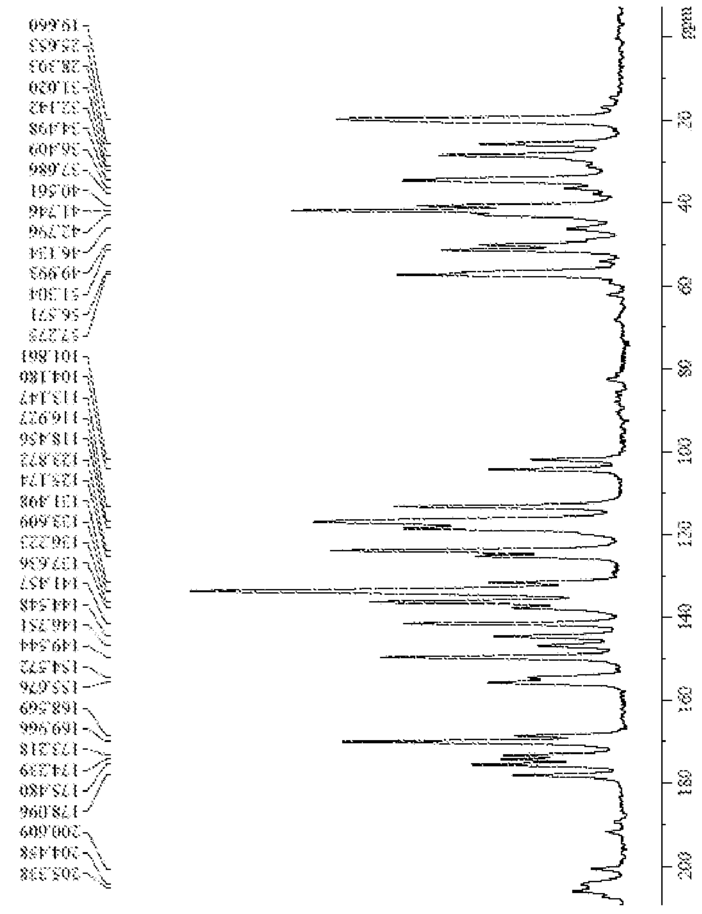

Figure 8b: $^{13}C$ solid state NMR spectrum of Form GT1 of Glasdegib Maleate (at the range of 0-100 ppm)
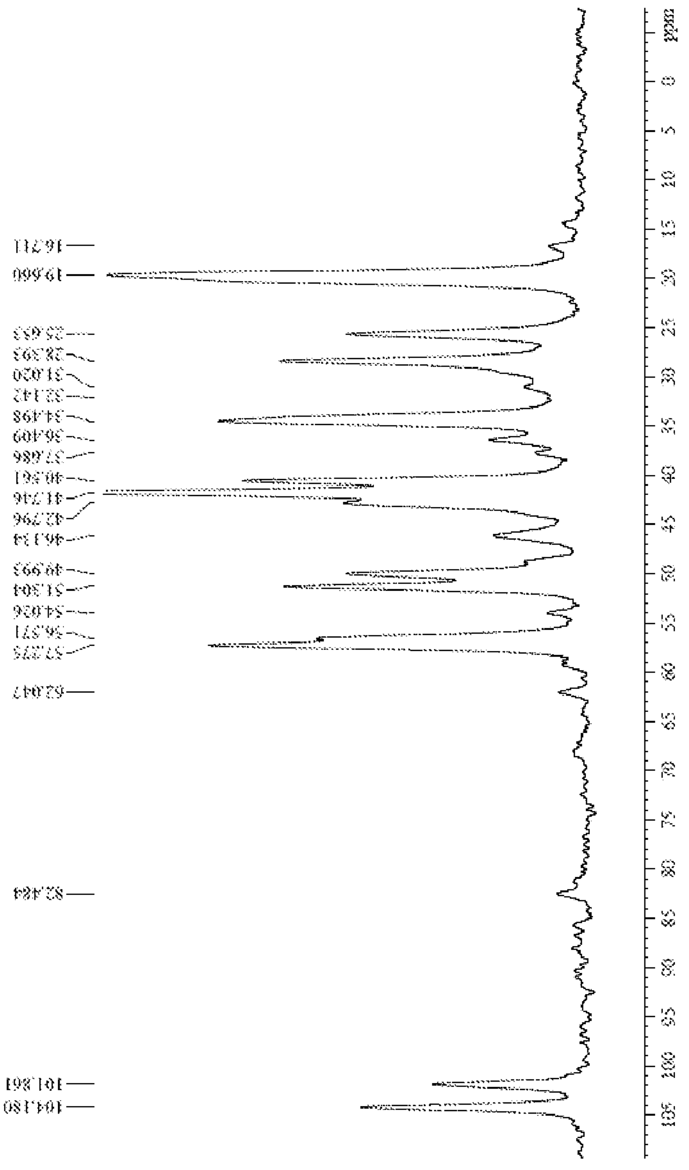

Figure 8c : $^{13}C$ solid state NMR spectrum of Form GT1 of Glasdegib Maleate (at the range of 100-200 ppm)
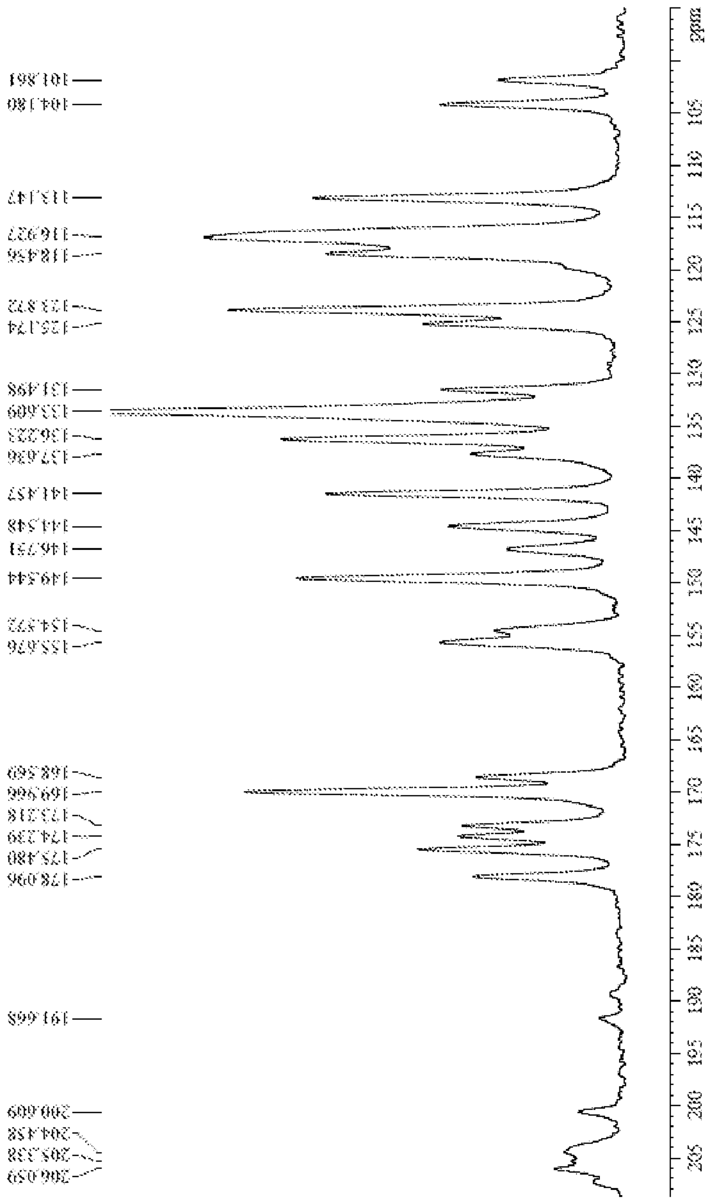

Figure 9a: $^{13}C$ solid state NMR spectrum of Form GT3 of Glasdegib Maleate (full scan)
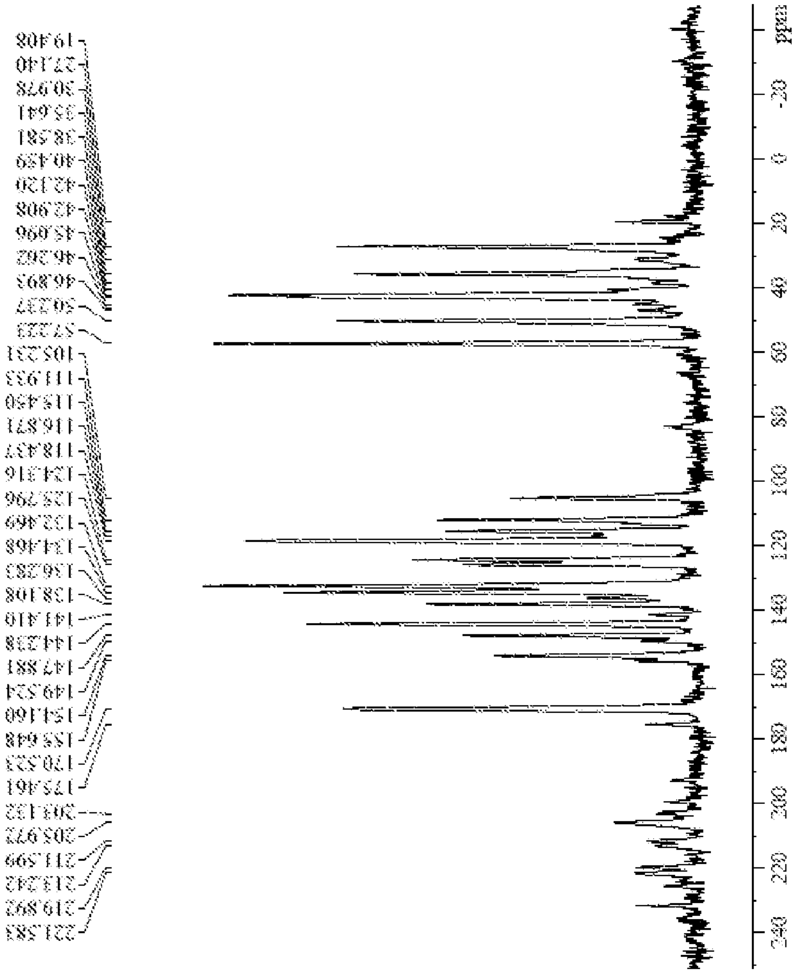

Figure 9b: $^{13}C$ solid state NMR spectrum of Form GT3 of Glasdegib Maleate (at the range of 0-100 ppm)
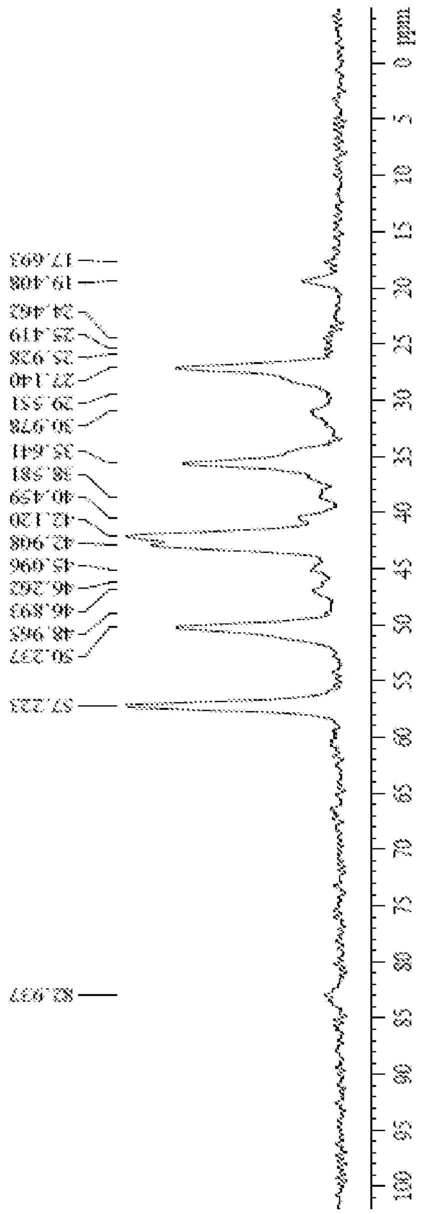

Figure 9c: $^{13}C$ solid state NMR spectrum of Form GT3 of Glasdegib Maleate (at the range of 100-200 ppm)
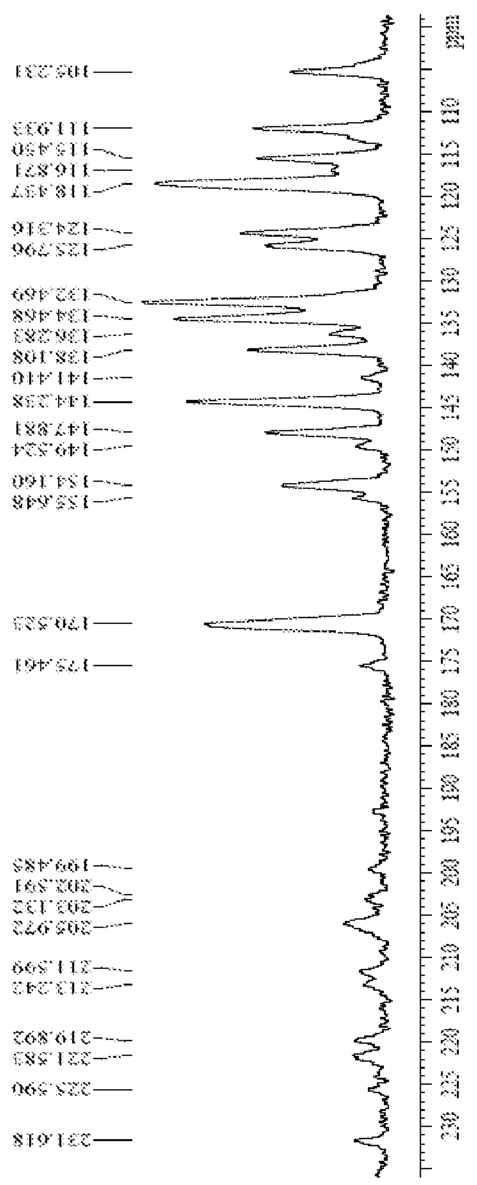

PROCESSES FOR THE PREPARATION OF GLASDEGIB AND SALT THEREOF AND SOLID STATE FORMS OF GLASDEGIB MALEATE AND PROCESS FOR PREPARATION THEREOF

CROSS REFERENCE TO RELATED APPLICATIONS

This application is a National Stage of, and claims priority to and the benefit of, International Patent Application No. PCT/US2021/015352, filed Jan. 28, 2021, which, in turn, claims the benefit of and priority to, Indian Provisional Application No. 202011003718, filed Jan. 28, 2020; Indian Provisional Application No. 202011010330, filed Mar. 11, 2020; and Indian Provisional Application No. 202011027219 filed Jun. 26, 2020, the entire disclosures of each of which are incorporated by reference herein.

FIELD OF THE DISCLOSURE

The present disclosure relates to safe and efficient processes for the synthesis of Glasdegib or salts thereof, preferably Glasdegib Maleate. The present disclosure also encompasses solid state forms of Glasdegib maleate, in embodiments crystalline polymorphs of Glasdegib maleate, processes for preparation thereof, and pharmaceutical compositions thereof.

BACKGROUND OF THE DISCLOSURE

Glasdegib maleate, 1-((2R,4R)-2-(1H-benzo[d]imidazol-2-yl)-1-methylpiperidin-4-yl)-3-(4-cyanophenyl)urea maleate, has the following chemical structure:

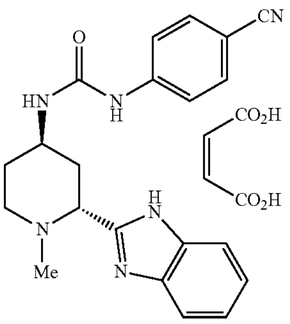

Glasdegib maleate is a hedgehog pathway inhibitor, and it is approved in combination with low-dose cytarabine for the treatment of newly-diagnosed acute myeloid leukemia (AML) in adult patients who are ≥75 years old or who have comorbidities that preclude use of intensive induction chemotherapy.

Glasdegib free base and its synthesis are disclosed in U.S. Pat. No. 8,148,401 (referred to herein as US ’401 or the ’401 patent) and Glasdegib maleate and its synthesis are disclosed in U.S. Pat. No. 10,414,748 (referred to herein as US ’748 or the ’748 patent). US ’401 discloses the synthesis of Glasdegib free base, which includes preparation of Glasdegib free base by reaction of a 4-isocyanatobenzonitrile with (2R,4R)-1-tert-butyl 2-methyl 4-aminopiperidine-1,2-dicarboxylate, followed by conversion of the obtained methoxy protected urea to acid, which is then reacted with Benzene-1,2-diamine to obtain amide which is then converted to Glasdegib free base. The process is illustrated by the following Scheme 1.

Scheme 1

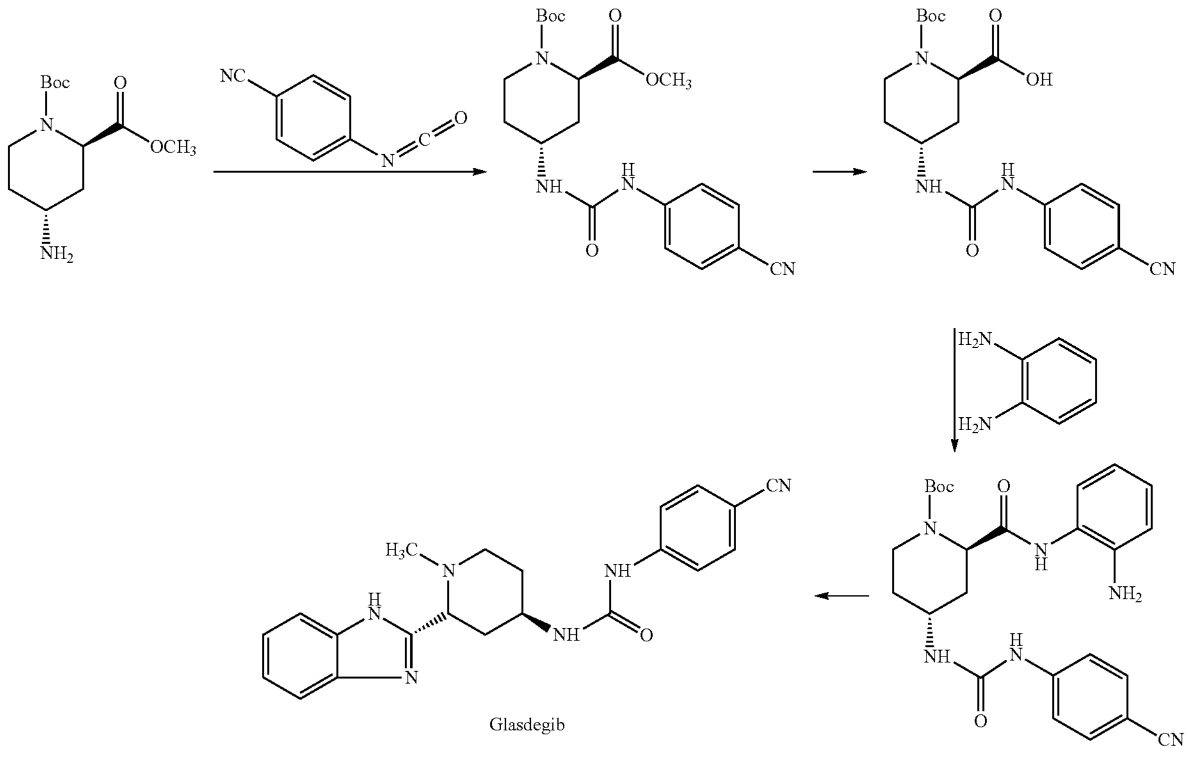

Glasdegib

US '748 discloses the synthesis of Glasdegib maleate, which includes preparation of Glasdegib maleate by reaction of 4-aminobenzonitrile with 1,1'-Carbonyldiimidazole, followed by reaction of the obtained amide imidazole complex with amine to obtain Glasdegib imidazole complex (1:1), which is then reacted with Maleic acid to obtain Glasdegib maleate. US '748 discloses the synthesis of Glasdegib maleate by reaction of Glasdegib free base with Maleic acid. The process is illustrated by the following Scheme 2.

Scheme-2

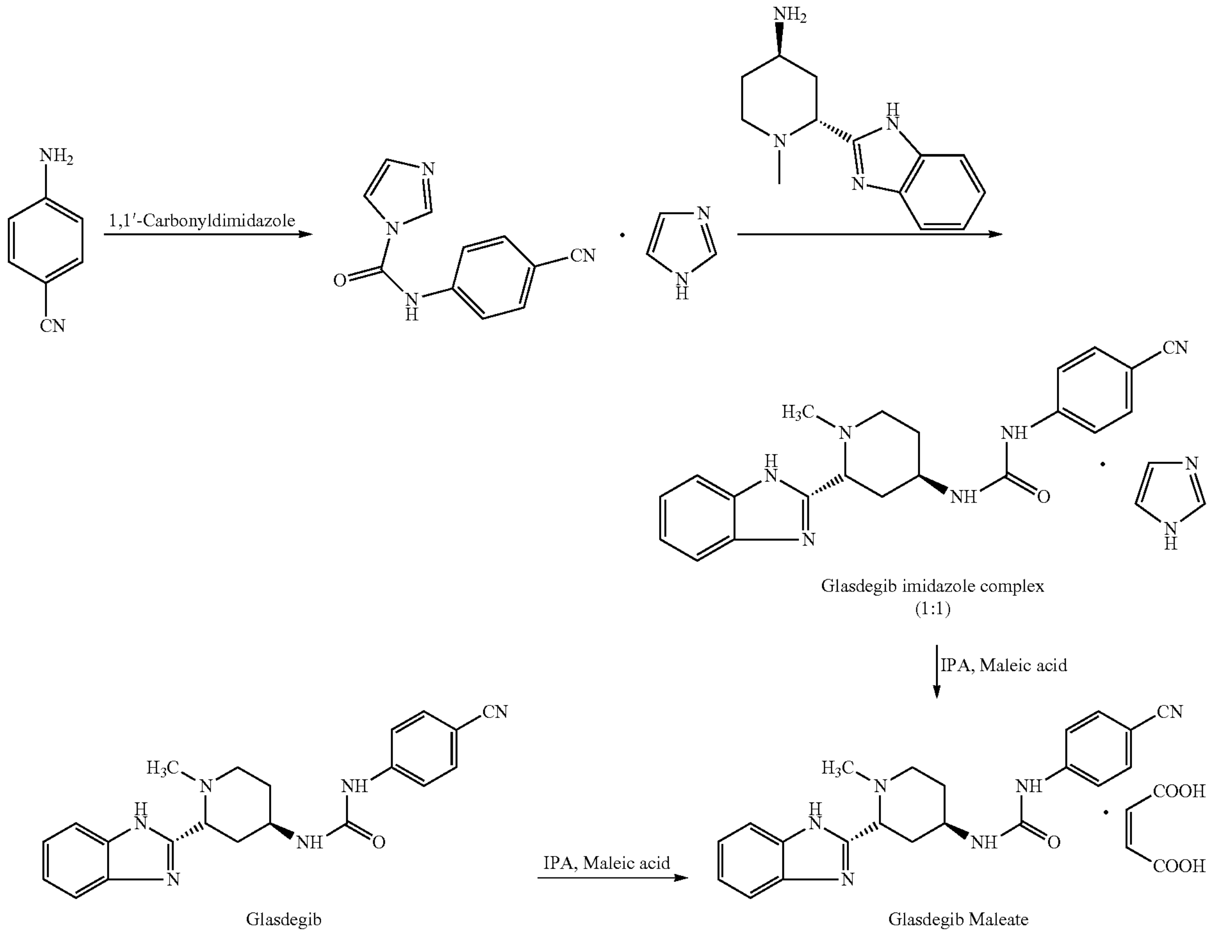

Accordingly, there is a need for additional processes allowing the efficient and safe synthesis of Glasdegib or salts thereof, preferably Glasdegib Maleate.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Glasdegib Maleate.

SUMMARY OF THE DISCLOSURE

The present disclosure relates to novel, safe and efficient process for the synthesis of Glasdegib or salts thereof, preferably Glasdegib Maleate.

In another aspect, the present disclosure provides Glasdegib or salts thereof, preferably Glasdegib Maleate produced by the process of the present disclosure.

In another aspect, the present disclosure provides Glasdegib produced by the processes of the present disclosure for use in preparation of Glasdegib salts, preferably Glasdegib maleate.

Glasdegib, Glasdegib salts, particularly Glasdegib maleate, prepared by the process of the present disclosure may be used for preparing pharmaceutical formulations and/or medicaments, preferably for treating acute myeloid leukemia.

The present disclosure provides crystalline polymorphs of Glasdegib maleate, processes for preparation thereof, and pharmaceutical compositions thereof. These crystalline polymorphs can be used to prepare other solid state forms of Glasdegib maleate, and their solid state forms.

The present disclosure also provides uses of the said solid state forms of Glasdegib maleate in the preparation of other solid state forms of Glasdegib maleate thereof.

The present disclosure provides crystalline polymorphs of Glasdegib maleate for use in medicine, including for the treatment of acute myeloid leukemia.

The present disclosure also encompasses the use of crystalline polymorphs of Glasdegib maleate of the present disclosure for the preparation of pharmaceutical compositions and/or formulations.

In another aspect, the present disclosure provides pharmaceutical compositions comprising crystalline polymorphs of Glasdegib maleate according to the present disclosure.

The present disclosure includes processes for preparing the above mentioned pharmaceutical compositions. The processes include combining any one or a combination of the crystalline polymorphs of Glasdegib maleate with at least one pharmaceutically acceptable excipient.

The crystalline polymorphs of Glasdegib maleate as defined herein and the pharmaceutical compositions or formulations of the crystalline polymorph of Glasdegib maleate may be used as medicaments, such as for the treatment of acute myeloid leukemia.

The present disclosure also provides methods of treating acute myeloid leukemia, by administering a therapeutically effective amount of any one or a combination of the crystalline polymorphs of Glasdegib maleate of the present disclosure, or at least one of the above pharmaceutical compositions, to a subject suffering from acute myeloid leukemia, or otherwise in need of the treatment.

The present disclosure also provides uses of crystalline polymorphs of Glasdegib maleate of the present disclosure, or at least one of the above pharmaceutical compositions, for the manufacture of medicaments for treating e.g., acute myeloid leukemia.

BRIEF DESCRIPTION OF THE DRAWINGS

FIG. 1 shows a characteristic X-ray powder diffraction pattern (XRPD) of Glasdegib maleate Form GT1;

FIG. 2 shows a characteristic XRPD of a Glasdegib maleate Form GT2;

FIG. 3 shows a characteristic XRPD of a Glasdegib maleate Amorphous Form;

FIG. 4 shows a characteristic XRPD of a Glasdegib Form A;

FIG. 5 shows a characteristic XRPD of a Glasdegib Amorphous Form;

FIG. 6 shows a characteristic XRPD of a Glasdegib maleate Form GT3;

FIG. 7 shows a characteristic XRPD of a Glasdegib maleate Form GT4;

FIG. 8*a* shows $^{13}C$ solid state NMR spectrum of Form GT1 of Glasdegib Maleate (full scan).

FIG. 8*b* shows $^{13}C$ solid state NMR spectrum of Form GT1 of Glasdegib Maleate (at the range of 0-100 ppm).

FIG. 8*c* shows $^{13}C$ solid state NMR spectrum of Form GT1 of Glasdegib Maleate (at the range of 100-200 ppm).

FIG. 9*a* shows $^{13}C$ solid state NMR spectrum of Form GT3 of Glasdegib Maleate (full scan).

FIG. 9*b* shows $^{13}C$ solid state NMR spectrum of Form GT3 of Glasdegib Maleate (at the range of 0-100 ppm).

FIG. 9*c* shows $^{13}C$ solid state NMR spectrum of Form GT3 of Glasdegib Maleate (at the range of 100-200 ppm).

DETAILED DESCRIPTION OF THE DISCLOSURE

The present disclosure relates to safe and efficient processes for the synthesis of Glasdegib or salts thereof, preferably Glasdegib Maleate.

The processes described in the literature have significant disadvantages. These processes involve the use of toxic reagents, such as 4-isocyanatobenzonitrile. In addition, 1,1'-Carbonyldiimidazole ("CDI") is used in previous processes which is sensitive to degradation by atmospheric moisture and is difficult to handle.

In contrast to the prior art processes, the processes of present disclosure do not involve use of toxic reagents, or of CDI. The process of the present disclosure is simple, economic and can be adapted to production in an industrial scale, i.e., greater than 1 kilogram scale.

As used herein, and unless indicated otherwise, the term "protecting group" refers to a grouping of atoms that when attached to a reactive functional group in a molecule masks, reduces or prevents reactivity of the functional group. Examples of protecting groups can be found in Greene and Wuts "Greene's Protective Groups in Organic Synthesis", 4th Edition, publ. Wiley, 2006 and Harrison et al., "Compendium of Synthetic Organic Methods", Vols. 1-8 (John Wiley and Sons, 1971-1996).

Representative amine protecting groups include, but are not limited to, those where the amine group is converted to carbamate or amide such as Fmoc, cbz, benzyl, trityl, Boc, trifluoroacetyl derivative, phthalic anhydride, or succinic anhydride derivative and sulfonic acid derivatives such as tosylate.

The present disclosure encompasses solid state forms of Glasdegib maleate, including crystalline polymorphs of Glasdegib maleate, processes for preparation thereof, and pharmaceutical compositions thereof.

Solid state properties of Glasdegib maleate and crystalline polymorphs thereof can be influenced by controlling the conditions under which Glasdegib maleate and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Glasdegib maleate described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Glasdegib maleate. In some embodiments of the disclosure, the described crystalline polymorph of Glasdegib maleate may contain from about 1% to about 20% (w/w), from about 5% to about 20% (w/w), or from about 5% to about 10% (w/w) of one or more other crystalline polymorph of the same Glasdegib maleate.

Depending on which other crystalline polymorphs a comparison is made, the crystalline polymorphs of Glasdegib maleate of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Glasdegib maleate referred to herein as being characterized by graphical data "as depicted in" or "as substantially depicted in" a Figure will thus be understood to include any crystal forms of Glasdegib maleate characterized with the graphical data having such small variations, as are well known to the skilled person, in comparison with the Figure.

As used herein, and unless stated otherwise, the term "anhydrous" in relation to crystalline forms of Glasdegib maleate, relates to a crystalline form of Glasdegib maleate which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to crystalline polymorph of Glasdegib maleate of the present disclosure corresponds to a crystalline polymorph of Glasdegib maleate that is physically separated from the reaction mixture in which it is formed.

As used herein, and unless indicated otherwise, the term "reduced pressure" refers to a pressure of about 10 mbar to about 500 mbar, or about 50 mbar.

As used herein, unless stated otherwise, the XRPD measurements are taken using copper Kα radiation wavelength 1.5418 Å (or 1.54 Å). XRPD peaks reported herein are measured using CuK α radiation, $\lambda$=1.5418 Å, typically at a temperature of 25±3° C.

As used herein, unless stated otherwise, $^{13}$C NMR reported herein are measured at 125 MHz at a magic angle spinning frequency $\omega_r/2\pi$=11 kHz, preferably at a temperature of at 293 K±3° K.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein and unless indicated otherwise, the term "ambient conditions" refer to atmospheric pressure and a temperature of 22-24° C.

As used herein, and unless indicated otherwise, the term "isolated" corresponds to compounds that are physically separated from the reaction mixture in which they are formed.

"Alkyl" refers to a monoradical of a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, iso-propyl, tert-butyl, sec-butyl, isobutyl, etc. Alkyl groups typically contain 1-10 carbon atoms, such as 1-6 carbon atoms or 1-4 carbon atoms, and can be substituted or unsubstituted.

"Alkyloxy" refers to a linear or branched, hydrocarbon group of formula —O-alkyl, in which the term "alkyl" is defined supra, and may include, e.g., a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

"Aryl" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. An aryl group may contain 6 (i.e., phenyl) or 9 to 15 ring atoms, such as 6 (i.e., phenyl) or 9-11 ring atoms, e.g., 6 (i.e., phenyl), 9 or 10 ring atoms.

"Alkylaryl" refers to an alkyl group in which a hydrogen atom is replaced by an aryl group, wherein alkyl group and aryl group are defined supra. Alkylaryl groups can be substituted or unsubstituted. Examples include, but are not limited to, benzyl ($C_6H_5CH_2$—).

"Alcohol protecting groups" refers to protecting groups which are introduced into a molecule by chemical modification of hydroxyl groups, for example to obtain chemoselectivity in a subsequent reaction. The term and use of protecting groups is well known in the art and for example described in Philipp J. Kocieński: *Protecting Groups,* 1. Auflage, Georg Thieme Verlag, Stuttgart 1994; Peter G. M. Wuts, Theodora W. Greene: *Green's Protective Groups in Organic Synthesis*, Fifth Ed. John Wiley & Sons Inc., Hoboken, New Jersey Alcohol protecting groups can be for example acetoxy groups, benzoyl groups (Bz), benzyl groups (Bn), β-methoxyethoxymethyl ether (MEM), [bis-(4-methoxyphenyl)phenylmethyl](DMT), methoxymethyl ether (MOM), [(4-methoxyphenyl)diphenylmethyl, (MMT), p-methoxybenzyl ether (PMB), methylthiomethyl ether, pivaloyl(Piv), tetrahydropyranyl (THP), triphenylmethyl(Tr), silyl ethers, trimethylsilyl ethers (TMS), triethylsilyl ethers (TES), tert-butyldimethylsilyl ethers (TBDMS), tri-iso-propylsilyloxymethyl ethers (TOM), triisopropylsilyl (TIPS) ethers, methyl ethers and ethoxyethyl ethers (EE).

The term "Amino" refers to the radical —NH2.

The term "Halogen" refers to chloro, bromo or Iodo.

The present disclosure provides for novel process for the synthesis of Glasdegib or salts thereof, preferably Glasdegib Maleate.

In one aspect, the present disclosure provides a process for preparation of Glasdegib or salts thereof, preferably Glasdegib Maleate, comprising a) reacting with 4-aminobenzonitrile of formula (2):

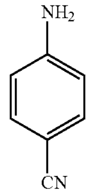

(2)

with compound of formula (III):

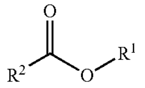

(III)

to obtain compound of formula (IV):

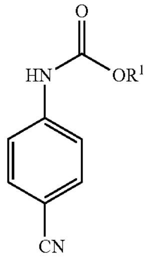

(IV)

wherein $R^1$ is a substituted or unsubstituted phenyl and $R^2$ is halogen;

b) reacting the compound of formula (IV)

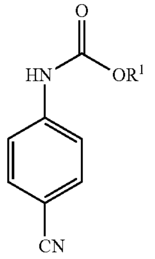

(IV)

with a compound of formula (5) or salt thereof (5)

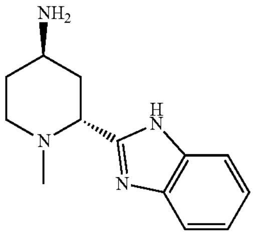

to obtain Glasdegib; and c) optionally converting Glasdegib to a salt thereof, preferably Glasdegib maleate.

In one embodiment $R^1$ is a substituted phenyl. In one embodiment substituted phenyl is selected from the group consisting of Methyl benzoyl, 4-Nitrophenyl, 4-methoxy phenyl, p-tolyl, 5-Isopropyl-3-methylphenyl. In another embodiment, $R^1$ is an unsubstituted phenyl, i.e., phenyl.

In one embodiment, halogen is Chloro, Bromo or Iodo. In embodiments, halogen is Chloro.

Step a) is typically carried out in the presence of one or more solvents, with or without suitable base. The solvent may be an aprotic solvent. Suitable solvents may include, for example, dichloromethane, ethyl acetate, isopropyl acetate, methyl acetate, acetonitrile, tetrahydrofuran, MTBE, Toluene, N-heptane, 2-Methyl THF. Optionally, the solvent may be toluene or dichloromethane. In embodiments, the solvent is dichloromethane. In other embodiments, the solvent is toluene. Suitable Base may include, for example, Organic or Inorganic Base. Organic base may include, but not limited to pyridine, piperidine, trimethylamine, diisopropylethylamine, n-methylmorpholine, diazabicycloundecene ("DBU"). Inorganic base may include, but not limited to sodium carbonate, sodium bicarbonate, potassium carbonate, potassium hydroxide, sodium hydroxide, potassium tert-Butoxide, potassium phosphate. In embodiments, the Base is pyridine. In embodiments, the reaction may be carried out in dichloromethane in the presence an organic base, particularly selected from pyridine, piperidine, trimethylamine, diisopropylethylamine, n-methylmorpholine, or diazabicycloundecene, and preferably pyridine. When a base is used, at the end of the reaction, a mineral acid, such as hydrochloric acid, may be added to neutralize the reaction mixture, and/or remove the base. In other embodiments, the reaction may be carried out in toluene, in the absence of an organic base.

In any embodiment of the process the reaction in step (a) may be carried out using a mole ratio of compound (2) to compound (III) of about 1:1.5 to about 1:0.80 or about 1:1.05.

Preferably, compound (III) is added to a solution of compound (2) in the solvent. The addition may be carried out at any suitable reaction temperature depending on the boiling point of the solvent. For example, compound (III) may be added to a dichloromethane solution of compound (2) at a temperature of about 20° C. to about 30° C., or to a toluene solution of compound (2) at a temperature of about 70° C. to about 85° C. In any embodiment, compound (III) may be phenyl chloroformate.

The resulting reaction mixture may be stirred at the same temperature as the addition temperature, or further heated and stirred. The reaction mixture may be heated to the reflux temperature, or close to (e.g., within about 0° C. to about 20° C., or about 5° C. to about 10° C.) the reflux temperature of the reaction mixture. The reaction mixture is stirred at the appropriate temperature until completion, for example as monitored by TLC or HPLC.

The product may be isolated by any suitable procedure, such as extraction, evaporation, evaporation and trituration, or antisolvent precipitation, and filtration.

In embodiments, in step a) the compound of formula (2) is reacted with phenyl chloroformate of formula (3) to obtain compound of formula (4), thereof, as illustrated by the following Scheme 3 (exemplified with $R^1$=phenyl and $R^2$=chloro).

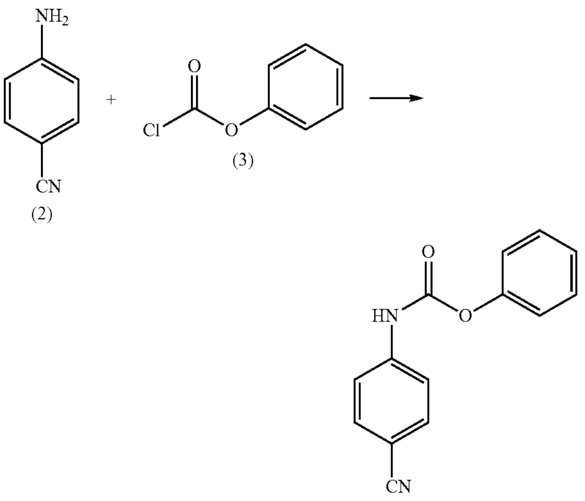

(2) (3) (4)

reacting the compound of formula (IV)

(IV)

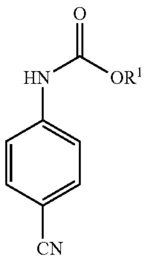

with a compound of formula (5) or salt thereof.

The reaction of the compound of formula (IV) with a compound of formula (5) or salt thereof in step b) is typically carried out in the presence of one or more solvents, and a suitable base. The solvent may be an aprotic solvent. Suitable solvents may include, for example, dichloromethane, ethyl acetate, isopropyl acetate, methyl acetate, acetonitrile, tetrahydrofuran, MTBE, Toluene, N-heptane, 2-Methyl THF, water or mixture thereof. In embodiments, the solvent is acetonitrile, 2-Methyl THE or tetrahydrofuran. Suitable base may include, for example, organic or inorganic base. Organic base may include, but not limited to pyridine, piperidine, triethylamine, trimethylamine, diisopropylethylamine, n-methylmorpholine, DBU. In embodiments, suitable base may include, for example, organic or inorganic base. Organic base may include, but not limited to pyridine, piperidine, trimethylamine, diisopropylethylamine, n-methylmorpholine, DBU. Inorganic base may include, but not limited to sodium carbonate, sodium bicarbonate, potassium carbonate, potassium hydroxide, sodium hydroxide, potassium tert-Butoxide, potassium phosphate. In embodiments, the base is triethylamine.

The reaction mixture may be heated to temperature of about 40° C. to reflux temperature of the reaction mixture, or about 45° C. to about 80° C. The reaction mixture may be stirred at the appropriate reaction temperature until completion, for example as monitored by TLC or HPLC. The product Glasdegib may be obtained from the reaction mixture basification. Isolation of the Glasdegib may be by any suitable procedure, such as cooling and filtering, extraction, evaporation and trituration, or antisolvent addition.

In some embodiments, in step b) the compound of formula (4) is reacted with compound of formula (5) to obtain Glasdegib of formula (1), as illustrated by the following Scheme 4 (exemplified with $R^1$=phenyl).

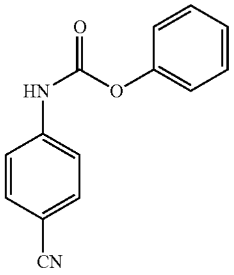

(4)

+

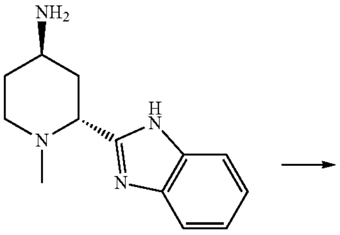

(5)

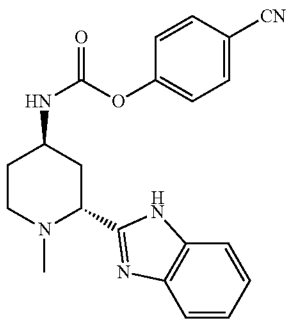

Glasdegib (1)

In some embodiments, in step b) the compound of formula (4) is reacted with tritosylate salt of compound of formula (5) to obtain Glasdegib of formula (1), as illustrated by the following Scheme 5 (exemplified with $R^1$=phenyl).

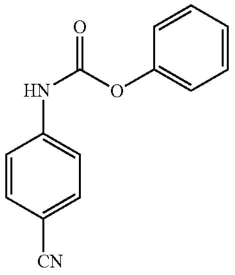

(4)

+

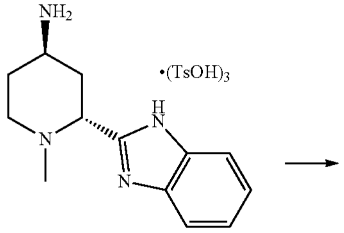

Tritosylate salt of (5)

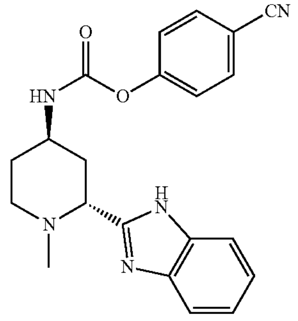

Glasdegib (1)

In one embodiment, the obtained Glasdegib is optionally converted to the Glasdegib maleate in the presence of Maleic acid. In any embodiment, the molar ratio of maleic acid to Glasdegib may be in the range of about 1:1 to about 1.8:1, about 1.1:1 to about 1.6:1, about 1.1 to about 1.5:1, or about 1.2 to about 1.5:1. The reaction can be carried out a suitable solvent. Suitable solvents are polar solvents, particularly protic solvents, such as alcohols, carboxylic acids and chlorinated hydrocarbons, particularly $C_1$-$C_6$ alcohols and $C_2$-$C_6$ carboxylic acids and $C_1$-$C_6$ chlorinated hydrocarbons; or $C_1$-$C_3$ alcohols, $C_2$-$C_4$ carboxylic acids, and $C_1$-$C_3$ chlorinated hydrocarbons. In embodiments, the solvent can be methanol, ethanol, 1-propanol, acetic acid, propionic acid, or dichloromethane, preferably acetic acid or dichloromethane, and more preferably acetic acid. In other embodiments, the solvent for the conversion of Glasdegib to Glasdegib maleate may be acetic acid. The maleic acid may be added either as a solid or as a solution, for example as a solution in the reaction solvent, to a solution of Glasdegib free base in the reaction solvent. The addition may be carried out at a temperature of between about 20° C. to about 90° C., about 22° C. to about 80° C., about 24° C. to about 60° C., or about 25° C. to about 50° C. In embodiments, the addition is carried out at a temperature of about 25° C. to about 50° C. The reaction mixture may be stirred at a temperature of about 20° C. to about 90° C., about 22° C. to about 80° C., about 24° C. to about 60° C., or about 25° C. to about 50° C. The stirring may be conducted for a period of about 30 minutes to about 6 hours, about 30 minutes to about 4 hours, about 30 minutes to about 3 hours, or about 45 minutes to about 2 hours. Optionally, an antisolvent may be added. Suitable antisolvents can be esters or ethers, such as $C_3$ to $C_8$ esters or $C_4$ to $C_8$ ethers. In embodiments, suitable antisolvents may be ethylacetate and methyl tert-butylether (MTBE). The mixture may be cooled prior to isolated Glasdegib maleate. In embodiments, the cooling may be to a temperature of about 10° C. to about 40° C., about 15° C. to about 35° C., or about 18° C. to about 32° C. The cooling may be carried out over a period of time, optionally about 30 minutes to about 3 hours, about 30 minutes to about 3 hours, or about 1 to 2 hours. Optionally, in embodiments, the mixture may be maintained at this temperature for an additional period, particularly a period of about 30 minutes to about 20 hours, about 30 minutes to about 17 hours, or about 1 to about 16 hours. Glasdegib maleate may be isolated by filtration, and optionally dried under reduced pressure. The drying may be carried out at a temperature of 30° C. to about 80° C., about 40° C. to about 75° C., or about 50° C. to about 70° C. The drying may be conducted over a period of about 2 to about 16 hours, about 2 to about 14 hours, or about 3 to about 12 hours.

Glasdegib or salts thereof, preferably Glasdegib maleate can be prepared starting from compound of formula (2) in situ without isolating the intermediates (4).

In one embodiment Glasdegib maleate can be prepared from Glasdegib by isolation or in situ without isolation of Glasdegib.

In one aspect, the present disclosure provides a process for preparation of Glasdegib or salts thereof, preferably Glasdegib Maleate comprising a) reacting the compound of formula (IV)

(IV)

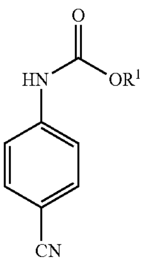

with compound of formula (5) or salt thereof (5)

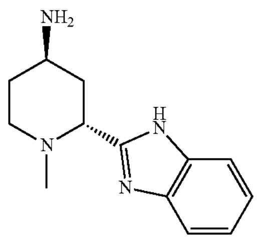

to obtain Glasdegib of formula (1)

Glasdegib (1)

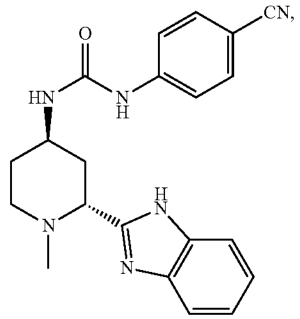

wherein $R^1$ is a substituted or unsubstituted phenyl; and b) optionally converting Glasdegib to a salt thereof, preferably Glasdegib maleate.

Glasdegib Maleate

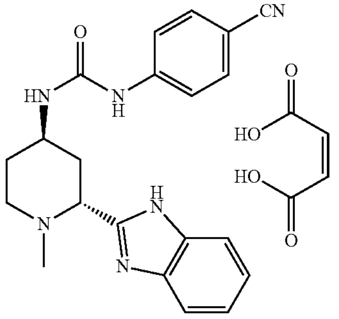

Steps (a) and (b) may be carried out by any of the procedures described herein above and below.

In one embodiment $R^1$ is a substituted. In one embodiment substituted phenyl is selected from the group consisting of Methyl benzoyl, 4-Nitrophenyl, 4-methoxy phenyl, p-tolyl, 5-Isopropyl-3-methylphenyl. In another embodiment R1 is an unsubstituted phenyl, i.e., phenyl.

Step a) is typically carried out in the presence of one or more solvents, and a suitable base. Suitable solvents may include, for example, dichloromethane, ethyl acetate, isopropyl acetate, methyl acetate, acetonitrile, tetrahydrofuran, MTBE, Toluene, N-heptane, 2-Methyl THF, water or mixture thereof. In embodiments, the solvent is acetonitrile or tetrahydrofuran. Suitable Base may include, for example, organic or Inorganic Base. Organic base may include, but not limited to pyridine, piperidine, trimethylamine, diisopropylethylamine, n-methylmorpholine, DBU. Inorganic base may include, but not limited to sodium carbonate, sodium bicarbonate, potassium carbonate, potassium hydroxide, sodium hydroxide, potassium tert-Butoxide, potassium phosphate. In embodiments, the base is trimethylamine In some embodiments, in step a) the compound of formula (4) is reacted with compound of formula (5) to obtain Glasdegib of formula (1), as illustrated by the following Scheme 4 (exemplified with R1=phenyl).

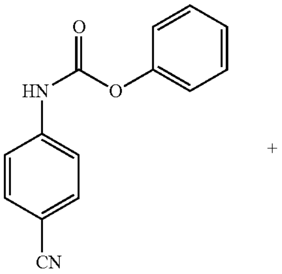

(4)

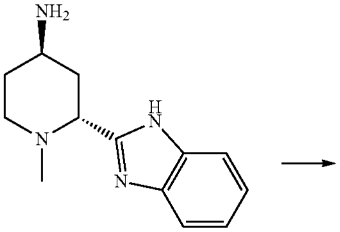

(5)

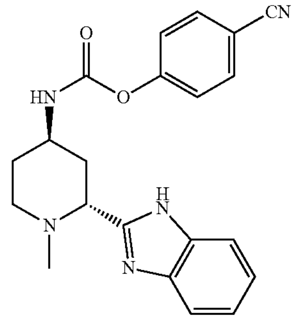

Glasdegib (1)

In some embodiments, in step a) the compound of formula (4) is reacted with tritosylate salt of compound of formula (5) to obtain Glasdegib of formula (1), as illustrated by the following Scheme 5 (exemplified with R1=phenyl).

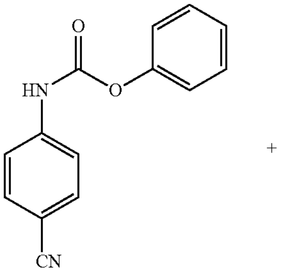

(4)

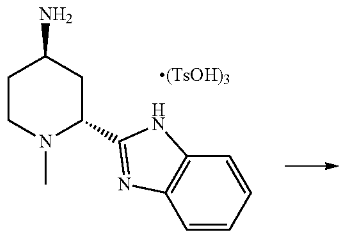

Tritosylate salt of (5)

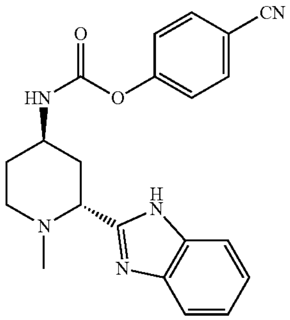

Glasdegib (1)

In one embodiment, the obtained Glasdegib is optionally converted to the Glasdegib maleate in the presence of Maleic acid.

In another embodiment, the Glasdegib Maleate is amorphous form.

In another embodiment, the Glasdegib Maleate is crystalline form.

In one embodiment, the Crystalline Glasdegib Maleate is Crystalline Glasdegib Maleate form GT1.

In one embodiment, the Crystalline Glasdegib Maleate is Crystalline Glasdegib Maleate form GT3.

Glasdegib or salts thereof, preferably Glasdegib maleate can be prepared starting from compound of formula (2) in situ without isolating the intermediates (4).

In one embodiment Glasdegib maleate can be prepared from Glasdegib by isolation or in situ without isolation of Glasdegib.

The general process for the preparation of Glasdegib or a salt thereof is shown in Scheme 6A below:
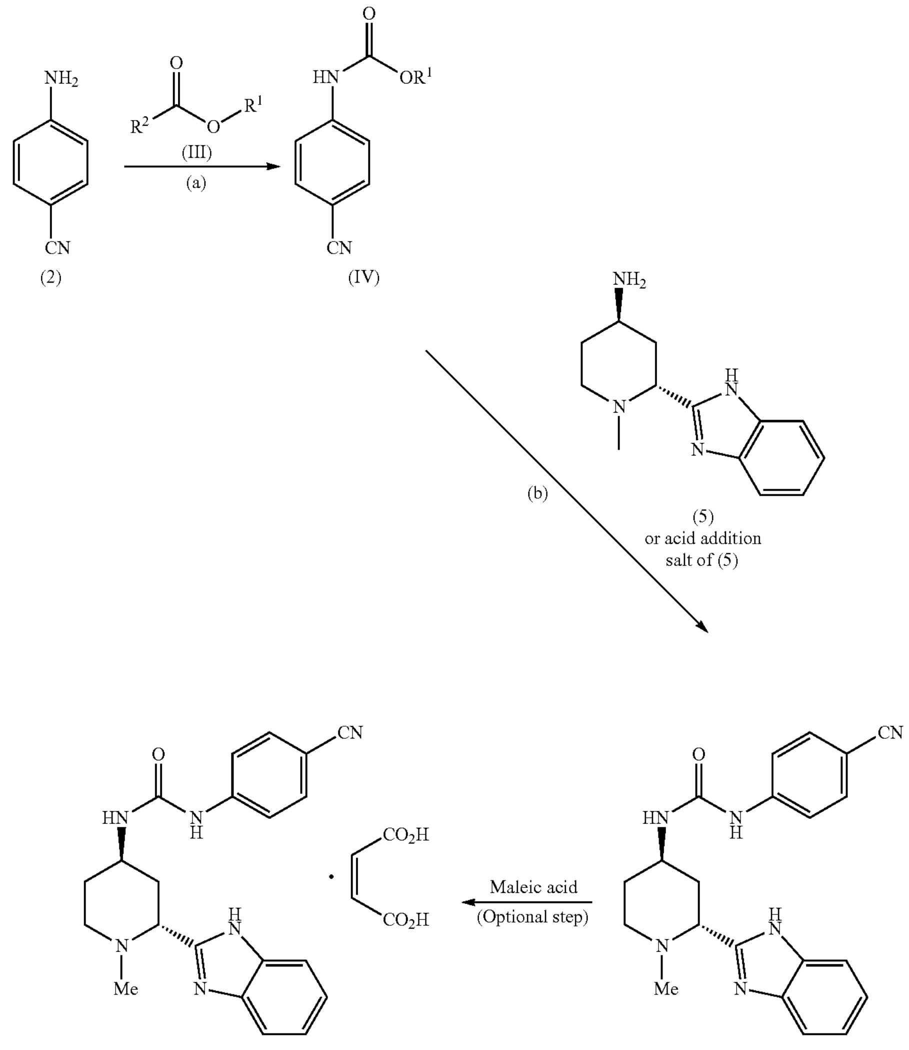
(2) (IV) (5) or acid addition salt of (5)
Glasdegib Maleate
Glasdegib (I)
An overview of the processes for preparation of Glasdegib or salts thereof, preferably Glasdegib maleate, according to an embodiment, is shown in Scheme 6B below.
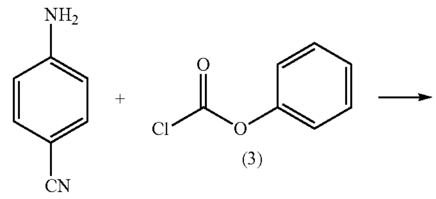
(2) (3)

-continued

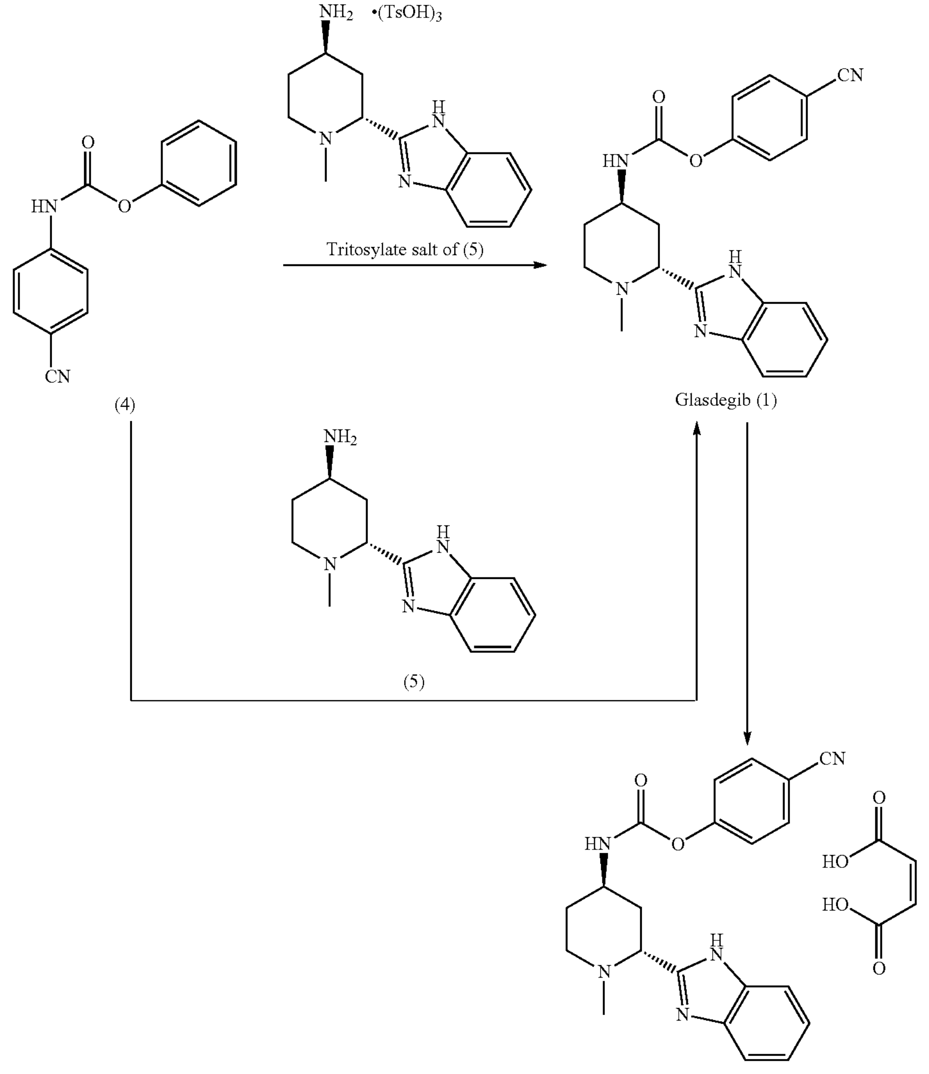

(4)

(5)

Glasdegib (1)

Glasdegib Maleate

In another aspect the present disclosure provides Glasdegib or salts thereof, preferably Glasdegib Maleate produced by the process of the present disclosure.

In another aspect of the present disclosure, there is provided a process as described in any aspect or embodiment disclosed herein further comprising combining the Glasdegib or Glasdegib maleate with at least one pharmaceutically acceptable excipient to form a pharmaceutical composition.

In another aspect the present disclosure provides Glasdegib produced by the processes of the present disclosure may be used to prepare salts of Glasdegib, preferably Glasdegib maleate. Such prepared Glasdegib and Glasdegib salts may be used to prepare pharmaceutical formulations and/or medicaments, particularly for the treatment of acute myeloid leukemia.

The present disclosure further includes crystalline forms of Glasdegib maleate as described herein. In any embodiment, the crystalline forms of Glasdegib maleate may be polymorphically pure or substantially free of any other solid state forms.

The present disclosure includes a crystalline polymorph of Glasdegib maleate, designated GT1. The crystalline Form GT1 of Glasdegib maleate may be characterized by data selected from one or more of the following: an X-ray powder diffraction pattern substantially as depicted in FIG. 1; an X-ray powder diffraction pattern having peaks at 7.0, 10.6, 14.1, 24.2 and 25.5 degrees 2-theta±0.2 degrees 2-theta; and combinations of these data; a solid state $^{13}C$ NMR spectrum having peaks at 101.9, 113.1, 116.9, 131.5, 136.2 and 149.5 ppm±0.2 ppm; a solid state $^{13}C$ NMR spectrum having the following chemical shift absolute differences from a reference peak at 57.3 ppm±2 ppm of 44.6, 55.8, 59.6, 74.2, 78.9 and 92.2 ppm±0.1 ppm; a solid state $^{13}C$ NMR spectrum substantially as depicted in FIG. 8*a*, 8*b* or 8*c*; and combinations of these data.

Crystalline Form GT1 of Glasdegib maleate may be further characterized by an X-ray powder diffraction pattern having peaks at 7.0, 10.6, 14.1, 24.2 and 25.5 degrees 2-theta 0.2 degrees 2-theta, and also having any one, two, three, four or five additional peaks selected from 11.3, 11.8, 13.3, 15.9, and 26.2 degrees 2-theta±0.2 degrees 2-theta.

Crystalline Form GT1 of Glasdegib maleate may be alternatively characterized by an X-ray powder diffraction pattern having peaks at 7.0, 10.6, 11.3, 11.8, 13.3, 14.1, 15.9, 24.2, 25.5 and 26.2 degrees 2-theta±0.2 degrees 2-theta.

In one embodiment of the present disclosure, crystalline Form GT1 of Glasdegib maleate is isolated.

In second embodiment crystalline Form GT1 of Glasdegib maleate can be isolated by crystallization.

In any embodiment, the crystalline Form GT1 of Glasdegib maleate may be polymorphically pure or substantially free of any other solid state forms.

The present disclosure further comprises a process for preparation of Form GT1, comprising crystallization of Glasdegib Maleate from acetic acid. The crystallization may comprise providing a solution of the Glasdegib Maleate in acetic acid and stirring the solution to obtain a slurry. The process for preparing crystalline Form GT1 of Glasdegib Maleate may further comprise isolating the said crystalline form. The isolation may be done, for example, by filtering the solid, for example by vacuum filtration and optionally drying.

In embodiments, the process includes the following steps:

(i) providing a solution of Glasdegib Maleate and acetic acid;
(ii) stirring; and
(iv) isolating Glasdegib Maleate Form GT1.

In any embodiment of the process, step (i) may be conducted at a temperature of about 15° C. to about 40° C., or about 18° C. to about 35° C., or about 20° C. to about 25° C. In any embodiment of this process, the acetic acid is typically used in an amount of about 10 to about 20, about 12 to about 18, or about 13 to about 15, or about 14 to about 14.5 ml per gram of Glasdegib Maleate.

In any embodiment of the process, stirring of step (ii) may be maintained, typically at the temperature about 15° C. to about 40° C., or about 18° C. to about 35° C., or about 20° C. to about 25° C. The stirring may be carried out for a period of about 10 hours to about 24 hours, about 14 hours to about 22 hours about 16 hours to about 20 hours, or about 18 hours.

The process may further include isolating the obtain Glasdegib Maleate Form GT1, for example by vacuum filtration. Following isolation, the Glasdegib Maleate Form GT1 may be dried. Glasdegib Maleate Form GT1 may be dried under reduced pressure, for any suitable time to remove the solvent, typically about 1 to about 10 hours, about 15 minutes to about 30 minutes.

The process may comprise preparing Glasdegib Maleate Form GT1 from Glasdegib free base in the suitable solvent. Thus, the mixture of Glasdegib Maleate in this process may be prepared by reacting a mixture of Glasdegib free base in the suitable solvent, such as acetic acid, with a solution of maleic acid in acetic acid. The solution of Glasdegib free base in the suitable solvent, such as acetic acid may comprise acetic acid in an amount of: about 1 to about 10, about 2 to about 8, or about 2.6 to about 6 ml of acetic acid per gm of Glasdegib. The molar ratio of maleic acid to Glasdegib in may be typically used 1:1 to about 1.8:1, about 1.1:1 to about 1.6:1, about 1.1 to about 1.5:1, or about 1.2 to about 1.5:1. The solution of maleic acid in acetic acid may comprise acetic acid in an amount of about 2 to about 18, about 4 to about 16, or about 6 to about 14 ml of acetic per gm of maleic acid. An antisolvent may be added to the mixture. In embodiments, the antisolvent can be ethyl acetate. The antisolvent may be used in an amount of about 8 to about 5 to about 27, about 9 to about 15, or about 10 to about 7 ml per gm of Glasdegib. Typically, the ratio of acetic acid to antisolvent is: about 1:2 to about 2:1, about 1:1.5 to about 1.5:1, about 1:1.2 to about 1.2:1, or about 1:1.1 to about 1:1.2, or about 1:1, or about 1:1.1.

Thus, this process may comprise:

(i) combining a solution of Glasdegib in a suitable solvent with solution of maleic acid in acetic acid (Pre dissolved maleic acid solution) to form a reaction mixture;
(ii) optionally seeding the reaction mixture;
(iii) adding suitable antisolvent to reaction mixture
(iv) cooling the reaction mixture; and
(v) isolating Glasdegib Maleate Form GT1.

The process may comprise combining a solution of the Glasdegib in the suitable solvent with solution of Maleic acid in acetic acid (Pre dissolved Maleic acid solution) to form a mixture comprising Glasdegib Maleate. The mixture of the Glasdegib Maleate in the suitable solvent may be in the form of a solution or a slurry. The reaction mixture may be optionally seeded with crystals of Form GT1 Glasdegib Maleate. The process for preparing crystalline Form GT1 of Glasdegib Maleate may further comprise adding suitable antisolvent to reaction mixture. The process for preparing crystalline Form GT1 of Glasdegib Maleate may further isolating the said crystalline form. The isolation may be done, for example, by filtering the solid, for example by vacuum filtration; optionally washing; and drying.

In any embodiment of the process, the mixture of Glasdegib Maleate in step (i) may be prepared by combining Glasdegib in the suitable solvent, typically at a temperature of about 20° C. to about 75° C., about 25° C. to about 60° C., or about 25° C. to about 55° C. In any embodiment of this process, the suitable solvent in step (i) may be acetic acid. In any embodiment of this process, the suitable solvent in step (i) is typically used in an amount of about 1 to about 10, about 2 to about 8, or about 2.5 to about 6 ml per gram of Glasdegib In any embodiment of the process, the solution of maleic acid the solvent (pre dissolved maleic acid solution) in step (i) may be prepared by combining maleic acid in the suitable solvent, typically at a temperature of about 20° C. to about 75° C., about 25° C. to about 60° C., or about 25° C. to about 55° C. In any embodiment of this process, the suitable solvent in step (i) may be the same solvent as used for preparing the solution of glasdegib, and is preferably acetic acid. In any embodiment of this process, the suitable solvent in step (i) is typically used in an amount of about 2 to about 18, about 4 to about 16, or about 6 to about 14 ml per gram of Maleic acid In any embodiment of this process, the molar ratio of maleic acid to Glasdegib in step (i) may be typically used 1:1 to about 1.8:1, about 1.1:1 to about 1.6:1, about 1.1 to about 1.5:1, or about 1.2 to about 1.5:1. In any embodiment of this process, the reaction mixture of step (i) may be prepared by combining a solution of Glasdegib in a suitable solvent with solution of Maleic acid in acetic acid (Pre dissolved maleic acid solution) typically at a temperature between about 20° C. to about 90° C., about 22° C. to about 80° C., about 24° C. to about 60° C., or about 25° C. to about 50° C. for period of about 30 minutes to about 6 hours, about 30 minutes to about 4 hours, about 30 minutes to about 3 hours, or about 45 minutes to about 2 hours. In any embodiment of the process, optionally acetic acid may be added to the Glasdegib maleate mixture and may be stirred at temperature of about 25° C. to about 30° C. for about 2 hours. In any embodiment of the process, optional seeding of the reaction mixture of step (ii) may be done at temperature of about 40° C. to about 50° C. In any embodiment of the process, addition of suitable antisolvent in reaction mixture of Glasdegib maleate in step (iii) may be done at temperature of about 40° C. to about 50° C. The reaction mixture of Glasdegib maleate in step (iii) may be optionally stirred at the temperature of about 40° C. to about 50° C. for period of about 30 minutes to 1 hour. In any embodiment of this process, the suitable antisolvent in step (iii) may be Ethyl acetate, MTBE.

In any embodiment of the process, the mixture may be cooled in step (iv), typically to a temperature of about 10° C. to about 40° C., about 15° C. to about 35° C., or about 18° C. to about 32° C. The cooling may be carried out over a period of time, optionally about 30 minutes to about 3 hours, about 30 minutes to about 3 hours, or about 1 to 2 hours. The mixture may be maintained, typically at this temperature for an additional period, particularly a period of about 30 minutes to about 20 hours, about 30 minutes to about 17 hours, or about 1 to about 16 hours.

The process may further include isolating form GT1 of Glasdegib maleate from the mixture, for example by vacuum filtration. Following isolation, the crystalline form GT1 of Glasdegib maleate may be optionally washed with suitable solvent such as MTBE, Acetic acid, EtOAc or mixture thereof. Following isolation, the crystalline form GT1 of Glasdegib maleate may be dried. The drying may be carried out at temperature of about The drying may be carried out at a temperature of 30° C. to about 80° C., about 40° C. to about 75° C., or about 50° C. to about 70° C. The drying may be conducted over a period of about 2 to about 16 hours, about 2 to about 14 hours, or about 3 to about 12 hours.

Crystalline Form GT1 of Glasdegib maleate may be an acetic acid solvate form. More preferably, Crystalline Form GT1 of Glasdegib maleate may be a diacetic acid solvate form. The acetic acid content in crystalline Form GT1 of Glasdegib maleate may be between about 16% to about 22% (w/w) as measured, for example, by HPLC. Typically, the acetic acid content in crystalline Form GT1 of Glasdegib maleate is not more than 21% (w/w) measured by typical method such as HPLC. In embodiments, the acetic acid content in crystalline Form GT1 of Glasdegib maleate is about 16% to about 22% (w/w), or about 16% to about 21% (w/w), or about 19% to about 21% (w/w) as measured by HPLC.

Crystalline Form GT1 of Glasdegib maleate may be characterized by each of the above characteristics alone/or by all possible combinations, e.g., an XRPD pattern having peaks at 7.0, 10.6, 14.1, 24.2 and 25.5 degrees 2-theta±0.2 degrees 2-theta; an XRPD pattern as depicted in FIG. 1, and combinations thereof.

The present disclosure includes a crystalline polymorph of Glasdegib maleate, designated GT2. The crystalline Form GT2 of Glasdegib maleate may be characterized by data selected from one or more of the following: an X-ray powder diffraction pattern substantially as depicted in FIG. 2; an X-ray powder diffraction pattern having peaks at 13.1, 18.0, 23.3, 24.4 and 25.9 degrees 2-theta±0.2 degrees 2-theta; and combinations of these data.

Crystalline Form GT2 of Glasdegib maleate may be further characterized by an X-ray powder diffraction pattern having peaks at 13.1, 18.0, 23.3, 24.4 and 25.9 degrees 2-theta±0.2 degrees 2-theta, and also having any one, two, three, four or five additional peaks selected from 4.8, 16.5, 19.5, 26.1 and 26.9 degrees 2-theta±0.2 degrees 2-theta.

Crystalline Form GT2 of Glasdegib maleate may be alternatively characterized by an X-ray powder diffraction pattern having peaks at 4.8, 13.1, 16.5, 18.0, 19.5, 23.3, 24.4 and 25.9, 26.1 and 26.9 degrees 2-theta±0.2 degrees 2-theta.

In one embodiment of the present disclosure, crystalline Form GT2 of Glasdegib maleate is isolated.

Crystalline Form GT2 of Glasdegib maleate may be a dimethyl carbonate solvate form.

In any embodiment, the crystalline Form GT2 of Glasdegib maleate may be polymorphically pure or substantially free of any other solid state forms.

Crystalline Form GT2 of Glasdegib maleate may be characterized by each of the above characteristics alone/or by all possible combinations, e.g., an XRPD pattern having peaks at 13.1, 18.0, 23.3, 24.4 and 25.9 degrees 2-theta±0.2 degrees 2-theta; an XRPD pattern as depicted in FIG. 2, and combinations thereof.

The present disclosure includes a crystalline polymorph of Glasdegib maleate, designated GT3. The crystalline Form GT3 of Glasdegib maleate may be characterized by data selected from one or more of the following: an X-ray powder diffraction pattern substantially as depicted in FIG. 6; an X-ray powder diffraction pattern having peaks at 6.3, 12.5, 13.7, 18.8 and 23.2 degrees 2-theta±0.2 degrees 2-theta; and combinations of these data; a solid state 13C NMR spectrum having peaks at 27.1, 50.2, 105.2, 144.2 and 170.5 ppm±0.2 ppm; a solid state 13C NMR spectrum having the following chemical shift absolute differences from a reference peak at 57.2 ppm±2 ppm of 30.1, 37.0, 48.0, 87.0 and 113.3 ppm±0.1 ppm; a solid state 13C NMR spectrum substantially as depicted in FIG. 9*a*, 9*b* or 9*c*; and combinations of these data.

Crystalline Form GT3 of Glasdegib maleate may be further characterized by an X-ray powder diffraction pattern having peaks at 6.3, 12.5, 13.7, 18.8 and 23.2 degrees 2-theta 0.2 degrees 2-theta, and also having any one, two or three additional peaks selected from 14.4, 20.1 and 21.1 degrees 2-theta±0.2 degrees 2-theta.

Crystalline Form GT3 of Glasdegib maleate may be alternatively characterized by an X-ray powder diffraction pattern having peaks at 6.3, 12.5, 13.7, 14.4, 18.8, 20.1, 21.1 and 23.2 degrees 2-theta±0.2 degrees 2-theta.

In one embodiment of the present disclosure, crystalline Form GT3 of Glasdegib maleate is isolated.

In second embodiment crystalline Form GT3 of Glasdegib maleate can be isolated by crystallization.

In any embodiment, the crystalline Form GT3 of Glasdegib maleate may be polymorphically pure or substantially free of any other solid state forms.

Crystalline Form GT3 of Glasdegib maleate may be characterized by each of the above characteristics alone/or by all possible combinations, e.g., an XRPD pattern having peaks at 6.3, 12.5, 13.7, 18.8 and 23.2 degrees 2-theta±0.2 degrees 2-theta; an XRPD pattern as depicted in FIG. 6, and combinations thereof.

The present disclosure further comprises a process for preparation of Form GT3, comprising crystallization of Glasdegib Maleate from dichloromethane. The crystallization may comprise providing a solution of the Glasdegib Maleate in dichloromethane and stirring the solution to obtain a solution. The process for preparing crystalline Form GT3 of Glasdegib Maleate may further comprise isolating the said crystalline form. The isolation may be done, for example, by filtering the solid, for example by vacuum filtration and optionally drying.

In embodiments, the process for preparation of Crystalline Form GT3 of Glasdegib Maleate includes the following steps:

(i) providing a solution of Glasdegib Maleate and dichloromethane;
(ii) stirring; and
(iii) isolating Glasdegib Maleate Form GT3.

In any embodiment of the process, step (i) may be conducted at a temperature of about 15° C. to about 40° C., or about 18° C. to about 35° C., or about 20° C. to about 25° C. In any embodiment of this process, the dichloromethane is typically used in an amount of: about 5 to about 15, about 8 to about 12, about 9 to about 11, or about 10 ml per gram of Glasdegib Maleate.

In any embodiment of the process, stirring of step (ii) may be maintained, typically at the temperature about 15° C. to about 40° C., or about 18° C. to about 35° C., or about 20° C. to about 25° C. The stirring may be conducted for a period of about 10 hours to about 48 hours, about 18 to about 36 hours, about 20 hours to about 30 hours, or about 24 hours.

The process may further include isolating the obtain Glasdegib Maleate Form GT3, for example by vacuum filtration. Following isolation, the Glasdegib Maleate Form GT3 may be dried. Glasdegib Maleate Form GT3 may be dried under reduced pressure, for any suitable time to remove the solvent, typically at temperature of about 40° C. to 50° C., or about 45° C.

Crystalline Form GT3 of Glasdegib maleate may be an acetic acid solvate form. More preferably, Crystalline Form GT3 of Glasdegib maleate may be a mono acetic acid solvate form. The acetic acid content in crystalline Form GT1 of Glasdegib maleate may be between about 8% to about 13% (w/w) as measured, for example, by HPLC. Typically, the acetic acid content in crystalline Form GT3 of Glasdegib maleate is not more than about 11% (w/w) measured by typical method such as HPLC. In embodiments, the acetic acid content in crystalline Form GT3 of Glasdegib maleate is about 8% to about 13% (w/w), or about 8% to about 11% as measured by HPLC. In embodiments, the acetic acid content in crystalline Form GT3 of Glasdegib maleate is about 9% to about 11% (w/w).

Crystalline Form GT3 of Glasdegib maleate may be characterized by each of the above characteristics alone/or by all possible combinations, e.g., an XRPD pattern having peaks at 6.3, 12.5, 13.7, 18.8 and 23.2 degrees 2-theta±0.2 degrees 2-theta; an XRPD pattern as depicted in FIG. 6, and combinations thereof.

The present disclosure includes a crystalline polymorph of Glasdegib maleate, designated GT4. The crystalline Form GT4 of Glasdegib maleate may be characterized by data selected from one or more of the following: an X-ray powder diffraction pattern substantially as depicted in FIG. 7; an X-ray powder diffraction pattern having peaks at 13.3, 14.8, 18.3, 19.5 and 22.8 degrees 2-theta±0.2 degrees 2-theta; and combinations of these data.

Crystalline Form GT4 of Glasdegib maleate may be further characterized by an X-ray powder diffraction pattern having peaks at 13.3, 14.8, 18.3, 19.5 and 22.8 degrees 2-theta±0.2 degrees 2-theta, and also having any one, two, three or four additional peaks selected from 6.1, 7.2, 16.4 and 29.3 degrees 2-theta±0.2 degrees 2-theta.

Crystalline Form GT4 of Glasdegib maleate may be alternatively characterized by an X-ray powder diffraction pattern having peaks at 6.1, 7.2, 13.3, 14.8, 16.4, 18.3, 19.5 and 22.8, and 29.3 degrees 2-theta±0.2 degrees 2-theta.

In one embodiment of the present disclosure, crystalline Form GT4 of Glasdegib maleate is isolated.

Crystalline Form GT4 of Glasdegib maleate may be a propionic acid solvate form.

In any embodiment, the crystalline Form GT4 of Glasdegib maleate may be polymorphically pure or substantially free of any other solid state forms.

Crystalline Form GT4 of Glasdegib maleate may be characterized by each of the above characteristics alone/or by all possible combinations, e.g., an XRPD pattern having peaks at 13.3, 14.8, 18.3, 19.5 and 22.8 degrees 2-theta±0.2 degrees 2-theta; an XRPD pattern as depicted in FIG. 7, and combinations thereof.

The above crystalline polymorphs can be used to prepare other crystalline polymorphs of Glasdegib maleate, and their solid state forms.

The present disclosure encompasses a process for preparing other solid state forms of Glasdegib maleate and their solid state forms thereof. The process includes preparing any one of the crystalline polymorph of Glasdegib maleate by the processes of the present disclosure.

The present disclosure provides the above described crystalline polymorphs of Glasdegib maleate for use in the preparation of pharmaceutical compositions comprising Glasdegib maleate and/or crystalline polymorphs thereof.

The present disclosure also encompasses the use of crystalline polymorphs of Glasdegib maleate of the present disclosure for the preparation of pharmaceutical compositions of crystalline polymorph Glasdegib maleate and/or crystalline polymorphs thereof.

The present disclosure includes processes for preparing the above mentioned pharmaceutical compositions. The processes include combining any one or a combination of the crystalline polymorphs of Glasdegib maleate of the present disclosure with at least one pharmaceutically acceptable excipient.

Pharmaceutical combinations or formulations of the present disclosure contain any one or a combination of the solid state forms of Glasdegib maleate of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Glasdegib maleate and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Glasdegib maleate can be administered. Glasdegib maleate may be formulated for administration to a mammal, in embodiments to a human, by injection. Glasdegib maleate can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs Glasdegib maleate and the pharmaceutical compositions and/or formulations of Glasdegib maleate of the present disclosure can be used as medicaments, in embodiments in the treatment of acute myeloid leukemia.

The present disclosure also provides methods of treating acute myeloid leukemia by administering a therapeutically effective amount of any one or a combination of the crystalline polymorphs of Glasdegib maleate of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

X-ray diffraction was performed on X-Ray powder diffractometer:

Bruker D8 Advance; CuK_radiation (λ=1.54 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

Scan range: 2-40 degrees 2-theta;
Scan mode: continuous;
Step size: 0.05 degrees;
Time per step: 0.5 s;
Sample spin: 30 rpm;
Sample holder: PMMA specimen holder ring.

All X-Ray Powder Diffraction peak values are calibrated with regard to standard silicon spiking in the sample.

SSNMR Method:

Solid-state NMR spectra were measured at 11.7 T using a Bruker Avance III HD 500 US/WB NMR spectrometer (Karlsruhe, Germany, 2013) with 3.2 mm probehead. The 13C CP/MAS NMR spectra employing cross-polarization were acquired using the standard pulse scheme at spinning frequency of 15 kHz and a room temperature (300 K). The recycle delay was 8 s and the cross-polarization contact time was 2 ms. The 13C scale was referenced to α-glycine (176.03 ppm for 13C). Frictional heating of the spinning samples was offset by active cooling, and the temperature calibration was performed with Pb(NO3)2. The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height Δv ½ was less than 3.5 Hz at 250 ms of acquisition time).

EXAMPLES

Preparation of Starting Materials

Glasdegib can be prepared according to methods known from the literature, for example WO 2009/004427 or as per below examples. Glasdegib maleate can be prepared according to methods known from the literature, for example WO 2016/170451 or as per below examples. The compound (5) can be prepared by known methods, for example, using the procedure described in Example 1 of U.S. Ser. No. 10/414,748. Compound (5) may be converted to the tritosylate salt by treatment with excess para-toluenesulfonic acid. Alternatively, compound (5)tritosylate salt may be prepared according to the procedures disclosed in Peng, Z., et al., Organic Letters, 2014, 16, 860-863 and supporting information S1-S19, page S5).

Example-1: Preparation of Phenyl(4-cyanophenyl)carbamate (Compound 4)

4-Aminobenzonitrile (compound 2, 5 gram), pyridine (6 gram) and Dichloromethane (100 ml) are added in flask. Phenyl chloroformate (5.5 ml) was added slowly at temperature of about 20° C. to about 30° C. The reaction mass was stirred at temperature of about 20° C. to about 30° C. and 2N HCl was added and stirred for a period of about 30 minutes. The layers were separated and the organic layer was concentrated completely. n-Heptane (50 ml) was added and the mixture was stirred for period of about 30 minutes. The reaction mass was filtered and the isolated solid was washed with n-Heptane (15 ml) and was dried under vacuum at a temperature of about 50° C. for period of about 4 hours to about 6 hours to obtain phenyl(4-cyanophenyl)carbamate (Compound 4). (Yield: 97.36%)

Example-2: Preparation of Glasdegib (Compound 1)

(2R,4R)-2-(1H-benzo[d]imidazol-2-yl)-1-methylpiperidin-4-amine tritosylate (tritosylate salt of Compound 5, 2 gram), phenyl(4-cyanophenyl)carbamate (Compound 4, 0.63 gram) and Triethylamine (1 gram) were added in acetonitrile (50 ml). The reaction mass was heated to a temperature of about 80° C. and was stirred for a period of about 3 hours. The reaction mass was cooled down to a temperature of about 50° C. and the solvent was distilled completely. Then, 2-methyl THF (20 ml) and 5% Aq. NaOH solution (10 ml) was added into the mass. The reaction mass was stirred for period of about for 30 minutes. The layers were separated, the organic layer was washed with 5% Aq. NaOH solution (10 ml), 2-Methyl THF (20 ml) was added to organic layer and organic layer was washed with water (10 ml). The solvents were distilled and acetonitrile (10 ml) was added to the mass. The reaction mass was heated to temperature of about 60° C. and was stirred for period of about 30 minutes. The reaction mass was cooled to a temperature of about 20° C. to about 25° C. and was stirred for period of about 2 hours. The solid was isolated by filtration and washed with acetonitrile (2 ml), then dried under vacuum at temperature of about 55° C. for period of about 4 hours to about 6 hours to obtain Glasdegib (Yield: 66%; HPLC Purity: 98.81%)

Example 3: Preparation of Glasdegib (Compound 1)

(2R,4R)-2-(1H-benzo[d]imidazol-2-yl)-1-methylpiperidin-4-amine tritosylate (tritosylate salt of Compound 5, 0.5 gram), phenyl(4-cyanophenyl)carbamate (Compound 4, 0.16 gm) and Triethylamine (0.27 gm) were added in acetonitrile (6 ml). The reaction mass was heated to a temperature of about 50° C. and was stirred for a period of about 3 hours. The reaction mass was cooled down to a temperature of about 50° C. and the solvent was distilled completely. Then, 2-methyl THE (6 ml) and 5% Aq. NaOH solution (6 ml) were added into the mass. The reaction mass was stirred for period of about for 30 minutes. The layers were separated, the organic layer was washed with 5% Aq. NaOH solution (10 ml), 2-Methyl THE (20 ml) was added to organic layer and organic layer was washed with water (6 ml). The solvents were distilled and acetonitrile (3 ml) was added to the mass. The reaction mass was heated to temperature of about 50° C. and was stirred for period of about 60 minutes. The reaction mass was cooled to a temperature of from about 20° C. to about 25° C. and was stirred for period of about 2 hours. The solid was isolated by filtration and washed with acetonitrile (0.5 ml), then dried under vacuum at temperature of about 50° C. for period of about 4 hours to about 6 hours to obtain Glasdegib. (Yield: 60%; HPLC Purity: 99.70%)

Example 4: Preparation of Glasdegib (Compound 1)

(2R, 4R)-2-(1H-benzo[d]imidazol-2-yl)-1-methylpiperidin-4-amine (Compound 5, 1.0 gm), phenyl(4-cyanophenyl) carbamate (Compound 4, 1.0 gm) and Triethylamine (0.43 gm) were added in tetrahydrofuran (10 ml). The reaction mass was heated to a temperature of about 55° C. and was stirred for a period of about 4 hours. The reaction mass was cooled down to temperature of about 25° C. Then, 2-methyl THE (10 ml) and 5% Aq. NaOH solution (10 ml) were added into the mass. The reaction mass was stirred for period of about for 30 minutes. The layers were separated, the organic layer was washed with 5% Aq. NaOH solution (10 ml), and Organic layer was washed with 5% brine solution (10 ml). The solvents were distilled and acetonitrile (8 ml) was added to the mass. The reaction mass was heated to temperature of about 50° C. and was stirred for period of about 60 minutes. The reaction mass was cooled to a temperature of about 20° C. to about 25° C. and was stirred for period of about 2 hours. The solid was isolated by filtration and washed with acetonitrile (2 ml), then dried under vacuum at temperature of about 50° C. for period of about 4 hours to about 6 hours to obtain Glasdegib (HPLC Purity: 97.45%)

Example-5: Preparation of Glasdegib Maleate

Glasdegib (100 mg) was added to isopropanol (2.2 ml). The reaction mass was heated to a temperature of about 55° C. to about 60° C. and Maleic acid (38 mg) was added and was stirred for a period of about 1 hour. Then, it was cooled to a temperature of about 20° C. to about 25° C. and it was stirred for period of about 2 hours. The solid was isolated by filtration, washed with isopropanol (0.2 ml) and dried under vacuum at temperature of about 55° C. to about 60° C. for period of about 4 hours to about 6 hours to obtain Glasdegib Maleate (Yield: 73%; HPLC Purity: 99.70%).

Example-6: Preparation of Phenyl(4-cyanophenyl)carbamate (Compound 4)

4-Aminobenzonitrile (compound 2, 100 gm) and toluene (1.0 L) were charged into reactor and was heated to temperature of about 70° C. to about 75° C. Phenyl chloroformate (140 gm) was added into it at 70-85° C. The reaction mass was heated to temperature of about 95° C. to about 105° C. and stirred for period of about 1 hours to about 2 hours. Then heated to temperature of about 109 to about 112° C. After completion of reaction, reaction mass was cooled and water (100 ml) was added and was stirred for period of about 0.5 hour to about 1.0 hour and at temperature of about 20° C. to about 30° C. The reaction mass was Filtered and isolated solid was washed with water followed by toluene (100 ml×2) and was dried under vacuum at temperature of about 45° C. to 55° C. to obtain phenyl(4-cyanophenyl)carbamate (Compound 4). (Yield: 88.12%; HPLC purity-99.52%)

Example-7: Preparation of Glasdegib (Compound 1)

(2R,4R)-2-(1H-benzo[d]imidazol-2-yl)-1-methylpiperidin-4-amine tritosylate (tritosylate salt of Compound 5, 200 gram), water (500 ml), Triethylamine (98 gm), phenyl(4-cyanophenyl)carbamate (Compound 4, 67 gm) and 2-Me-THF (600 ml) were added into reactor. The reaction mass was heated to temperature of about 45° C. to about 55° C. Stirred and reaction progress was monitored on HPLC. After completion of reaction, the reaction mass was cooled down to a temperature of about 20° C. to about 30° C. Organic Layer was separated. Aqueous Layer was extracted with 2-Methyl THF (400 ml) and both the organic layer were combined and washed with aq. NaOH solution at temperature of about 15° C. to about 25° C. Organic layer was neutralized with dilute aq, HCl solution and layers were separated. Organic layer was distilled out to make volume of about 1.0 volume to 2.0 volume, and stripped with ethyl acetate. Ethyl acetate (200 ml) was charged, and heated the mass at temperature of about 75° C. to about 80° C. Stirred for period of about 30 minutes to about 60 minutes and cooled to temperature of about 20° C. to about 30° C. The obtained solid was filtered and washed with ethyl acetate (200 ml), Suck dried for period of about 1 to 2 hours and dried under vacuum at temperature of about 50° C. to 60° C. to obtain Glasdegib (Yield: 75.30%%; HPLC purity 99.93%)

Example-8: Preparation of Glasdegib Maleate Form GT1

Glasdegib (60 gm) was dissolved in acetic acid (180 ml) at temperature of about 45° C. to about 55° C. The solution was filtered through micron filter and washed with acetic acid (30 ml) to get clear solution. Pre dissolved maleic acid solution [Maleic acid (22.2 gm) was dissolved in acetic acid (210 ml)] was added to above solution at temperature of about 40° C. to about 50° C. and stirred at same temperature for about 45 minutes. Seed of Glasdegib maleate Form GT1 was added to above solution and EtOAc (420 ml) was added slowly and was stirred at temperature of about 40° C. to about 50° C. for period of about 30 minutes to about 1 hour. Slowly cooled the reaction mass to temperature of about 20° C. to about 30° C. over the period of 1 hours to about 2 hours and maintained at temperature of about 20° C. to about 30° C. for period of 1 hours to about 2 hours. The obtained solid was filtered, washed with 5% mixture of Acetic acid in EtOAc (60 ml) and dried under vacuum at temperature of about 55° C. to 65° C. for period of about 8 hours to about 12 hours. Crystalline Glasdegib Maleate was obtained. A sample was analyzed by XRPD. Form GT1 was obtained. (Yield: 88.96%) HPLC purity-99.98%).

Example 9: Preparation of Glasdegib Maleate Form GT1

Glasdegib Maleate (Amorphous, 0.07 gram) was dissolved in acetic acid (1 mL) at temperature of about 20° C. to about 25° C. to get clear solution. The obtained clear solution was stirred at temperature of about 20° C. to about 25° C. for period of about 18 hours. The slurry mass was filtered and suck dried for a period of about 15 minutes to about 30 minutes. Crystalline Glasdegib Maleate was obtained. A sample was analyzed by XRPD. Form GT1 was obtained. An XRPD pattern is shown in FIG. 1.

Example 10: Preparation of Glasdegib Maleate Form GT2

Glasdegib Maleate (Amorphous, 0.07 gram) was added in dimethyl carbonate (1 mL) at temperature of about 20° C. to about 25° C. and slurry is obtained. The obtained slurry is stirred for a period of about 24 hours under magnetic stirring. The slurry mass was filtered and suck dried for a period of about 15 minutes to about 30 minutes. Crystalline Glasdegib Maleate was obtained. A sample was analyzed by XRPD. Form GT2 was obtained. An XRPD pattern is shown in FIG. 2.

Example 11: Preparation of Glasdegib Maleate Amorphous Form

Glasdegib Maleate (0.2 gram) was dissolved in methanol (20 mL) at temperature of about 25° C. to about 30° C. The solution was filtered. The obtained clear solution was subjected to distillation under reduced pressure at temperature of about 40° C. to about 45° C. for period of about 30 minutes to about 45 minutes and a solid was obtained. A sample was analyzed by XRPD. Amorphous form of Glasdegib maleate was obtained. An XRPD pattern is shown in FIG. 3.

Example 12: Preparation of Glasdegib Form A

Glasdegib (0.2 gram) was dissolved in dichloromethane (1 mL) and methanol (0.2 mL) solvent mixture at temperature of about 25° C. to about 30° C. in a test tube. The solution was filtered through 0.45 micron filter and the obtained clear solution was subjected to slow solvent evaporation at temperature of about 20° C. to about 25° C. The clear solution was covered with paraffin film with a pin hole for period of about 2 days. Crystalline Glasdegib was obtained. A sample was analyzed by XRPD. Form A was obtained. An XRPD pattern is shown in FIG. 4.

Example 13: Preparation of Glasdegib Form A

Glasdegib (0.15 gram) was dissolved in acetonitrile (60 mL) at temperature of about 40° C. to about 45° C. in a round bottom flask. The solution was filtered through 0.45 micron filter and the obtained clear solution was subjected to distillation under reduced pressure at temperature of about 50° C. to about 55° C. for period of about 30 minutes to about 45 minutes. Crystalline Glasdegib was obtained. A sample was analyzed by XRPD. Form A was obtained.

Example 14: Preparation of Glasdegib Amorphous Form

Glasdegib (0.2 gram) was dissolved in methanol (5 mL) at temperature of about 25° C. to about 30° C. in a round bottom flask. The solution was filtered through 0.45 micron filter. The obtained clear solution was subjected to distillation under reduced pressure at temperature of about 40° C. to about 45° C. for period of about 30 minutes to about 45 minutes and a solid was obtained. A sample was analyzed by XRPD. Amorphous form of Glasdegib was obtained. An XRPD pattern is shown in FIG. 5.

Example 15: Preparation of Glasdegib Amorphous Form

Glasdegib (0.1 gram) was dissolved in 1% methanol in dichloromethane solvent mixture (30.3 mL) at temperature of about 40° C. to about 45° C. in a round bottom flask. The solution was filtered through 0.45 micron filter. The obtained clear solution was subjected to distillation under reduced pressure at temperature of about 40° C. to about 45° C. for period of about 30 minutes to about 45 minutes and a solid was obtained. A sample was analyzed by XRPD. Amorphous form of Glasdegib was obtained.

Example 16: Preparation of Glasdegib Maleate Form GT3

Glasdegib Maleate Form GT1 (300 mg) was dissolved in dichloromethane (3 mL) at temperature of about 20° C. to about 25° C. to get clear solution. The obtained clear solution was stirred at temperature of about 20° C. to about 25° C. The solid was precipitated in period of about 2 minutes to about 3 minutes and was stirred for period of about 24 hours at temperature of about 20° C. to about 25° C. The obtained solid was filtered, washed with dichloromethane (1.0 mL) and dried under vacuum at temperature of about 45° C. Crystalline Glasdegib Maleate was obtained. A sample was analyzed by XRPD. Form GT3 was obtained (Yield: 170 mg; HPLC Purity: 99.95%). An XRPD pattern is shown in FIG. 6.

Example 17: Preparation of Glasdegib Maleate Form GT4

Glasdegib Maleate (Amorphous; 70 mg) was dissolved in propionic acid (0.3 ml) at temperature of about 60° C. to get clear solution. Cyclohexane (1.5 ml) was added slowly at temperature of about 20° C. to about 30° C. and was stirred at temperature of about 20 to about 25° C. for overnight. The obtained solid was filtered and suck dried for a period of about 15 minutes to about 20 minutes. Crystalline Glasdegib Maleate was obtained. A sample was analyzed by XRPD. Form GT4 was obtained. An XRPD pattern is shown in FIG. 7.

Example 18: Preparation of Glasdegib Maleate Form GT1

Glasdegib (5 g) was dissolved in acetic acid (15 mL) at temperature of about 40° C. to about 45° C. The solution was filtered through cotton and cotton was washed with acetic acid (2.5 mL) to get clear solution. Pre dissolved maleic acid solution [Maleic acid (1.9 g) was dissolved in acetic acid (15 mL) and filtered through cotton and cotton was washed with acetic acid (2.5 mL)] was added to above solution at temperature of about 40° C. to about 45° C. and stirred at same temperature for about 45 minutes. Seed of Glasdegib maleate Form GT1 was added to above solution and MTBE (70 mL) was added slowly and was stirred for period of about 1.0 hour at temperature of about 40° C. to about 45° C., cooled to temperature of about 24° C. to about 30° C. and stirred for period of about 2 hours. The obtained solid was filtered, washed twice with MTBE (10 mL) and dried under vacuum at temperature of about 50° C. for period of about 6 hours. Crystalline Glasdegib Maleate was obtained. A sample was analyzed by XRPD. Form GT1 was obtained. (Yield: 7.12 g; HPLC purity: 99.82%).

Example 19: Preparation of Glasdegib Maleate Form GT1

Glasdegib (1.0 g) was dissolved in acetic acid (5 ml) at temperature of about 25° C. to get clear solution. Pre dissolved maleic acid solution [Maleic acid (0.37 g) was dissolved in 5 mL of acetic acid] was added into above solution. Acetic acid (3.5 mL) was added to the solution and stirred for period of about 2.0 hours at temperature of about 25° C. to about 30° C. The temperature of the solution was increased to about 40° C. and MTBE (27 mL) was added slowly to it. The solution was cooled to temperature of about 20° C. to about 25° C. and stirred for period of about 1 hour. The solid precipitate was observed and stirred for period of about 16 hours at temperature of about 20° C. to about 25° C. The obtained solid was filtered, washed with MTBE (10 mL) and dried under vacuum at temperature of about 58° C. for period of about 6 hours. A sample was analyzed by XRPD. Form GT1 was obtained. (Yield: 1.22 g; HPLC purity: 99.41%).

Example 20: Preparation of Glasdegib Maleate Amorphous Form

Glasdegib Maleate Form GT1 (0.6 gram) was dissolved in methanol (70 mL) at temperature of about 25° C. to about 30° C. The solution was filtered. The obtained clear solution was subjected to distillation and degassed under reduced pressure at temperature of about 55° C. for period of about 1.0 hr. A sample was analyzed by XRPD. Amorphous form of Glasdegib maleate was obtained. (Yield: 0.45 g; HPLC Purity: 99.40%).

Example 21: Preparation of Glasdegib (Compound 1)

(2R,4R)-2-(1H-benzo [d]imidazol-2-yl)-1-methylpiperidin-4-amine tritosylate (tritosylate salt of Compound 5, 0.5 gram), phenyl(4-cyanophenyl)carbamate (Compound 4, 0.16 gm) and Triethylamine (0.27 gm) were added in acetonitrile (6 ml). The reaction mass was heated to a temperature of about 50° C. and was stirred for a period of about 3 hours, and the solvent was distilled completely. Then, 2-methyl THE (6 ml) and 5% Aq. NaOH solution (6 ml) were added into the mass. The reaction mass was stirred for period of about for 30 minutes. The layers were separated, the organic layer was washed with 5% Aq. NaOH solution (10 ml), 2-Methyl THE (20 ml) was added to organic layer and organic layer was washed with water (6 ml). The solvents were distilled and acetonitrile (3 ml) was added to the mass. The reaction mass was heated to temperature of about 50° C. and was stirred for period of about 60 minutes. The reaction mass was cooled to a temperature of from about 20° C. to about 25° C. and was stirred for period of about 2 hours. The solid was isolated by filtration and washed with acetonitrile (0.5 ml), then dried under vacuum at temperature of about 50° C. for period of about 4 hours to about 6 hours to obtain Glasdegib. (Yield: 60%; HPLC Purity: 99.70%).

The invention claimed is:

1. A crystalline form of Glasdegib Maleate characterized by data selected from one or more of the following:

a) an XRPD pattern having peaks at 7.0, 10.6, 14.1, 24.2 and 25.5 degrees 2-theta±0.2 degrees 2-theta;

b) an XRPD pattern as depicted in FIG. 1;

c) a solid state $^{13}C$ NMR spectrum having peaks at 101.9, 113.1, 116.9, 131.5, 136.2 and 149.5 ppm±0.2 ppm;

d) a solid state $^{13}C$ NMR spectrum having the following chemical shift absolute differences from a reference peak at 57.3 ppm±2 ppm of 44.6, 55.8, 59.6, 74.2, 78.9 and 92.2 ppm±0.1 ppm;

e) a solid-state $^{13}C$ NMR spectrum substantially as depicted in FIG. *8a*, *8b* or *8c*; and f) combinations of two or more of: a, b, c, d, and e.

2. The crystalline form of Glasdegib Maleate according to claim 1, which is characterized by an XRPD pattern having peaks at 7.0, 10.6, 14.1, 24.2 and 25.5 degrees 2-theta±0.2 degrees 2-theta, and also having one, two, three, four, or five additional peaks selected from 11.3, 11.8, 13.3, 15.9, and 26.2 degrees two theta±0.2 degrees two theta.

3. The crystalline form of Glasdegib Maleate according to claim 1, which is characterized by an XRPD pattern having peaks at 7.0, 10.6, 11.3, 11.8, 13.3, 14.1, 15.9, 24.2, 25.5, 26.2 degrees 2-theta±0.2 degrees 2-theta.

4. The crystalline form of Glasdegib Maleate according to claim 1, wherein said crystalline form is an acetic acid solvate.

5. The crystalline form of Glasdegib Maleate according to claim 1, which contains no more than about 20% of any other crystalline forms of Glasdegib Maleate.

6. The crystalline form Glasdegib Maleate according to claim 1, which contains no more than about 20% of amorphous Glasdegib Maleate.

7. A pharmaceutical composition comprising the crystalline form of Glasdegib Maleate according to claim 1.

8. A pharmaceutical formulation comprising the crystalline form of Glasdegib Maleate according to claim 1, with at least one pharmaceutically acceptable excipient.

9. A process for preparing a pharmaceutical formulation comprising combining the crystalline form of Glasdegib Maleate according to claim 1 with at least one pharmaceutically acceptable excipient.

10. A method of treating acute myeloid leukemia, comprising administering a therapeutically effective amount of the crystalline form of Glasdegib Maleate according to claim 1, to a subject in need of the treatment.

* * * * *